(12) United States Patent
Lee et al.

(10) Patent No.: US 12,109,225 B2
(45) Date of Patent: Oct. 8, 2024

(54) METHODS FOR POTENTIATING CANCER TREATMENT USING IONIZING RADIATION

(71) Applicant: GLYCOMIRA THERAPEUTICS, INC., Salt Lake City, UT (US)

(72) Inventors: Won Yong Lee, Bountiful, UT (US); Thomas P. Kennedy, Williamsburg, VA (US); Glenn D. Prestwich, Spokane, WA (US)

(73) Assignee: GLYCOMIRA THERAPEUTICS, INC., Salt Lake City, UT (US)

( * ) Notice: Subject to any disclaimer, the term of this patent is extended or adjusted under 35 U.S.C. 154(b) by 550 days.

(21) Appl. No.: 17/293,103

(22) PCT Filed: Nov. 11, 2019

(86) PCT No.: PCT/US2019/060834
§ 371 (c)(1),
(2) Date: May 12, 2021

(87) PCT Pub. No.: WO2020/102137
PCT Pub. Date: May 22, 2020

(65) Prior Publication Data
US 2021/0401873 A1 Dec. 30, 2021

Related U.S. Application Data

(60) Provisional application No. 62/760,134, filed on Nov. 13, 2018.

(51) Int. Cl.
| | | |
|---|---|---|
| *A61K 38/00* | (2006.01) | |
| *A61K 31/737* | (2006.01) | |
| *A61K 41/00* | (2020.01) | |
| *A61N 5/10* | (2006.01) | |

(52) U.S. Cl.
CPC ........ *A61K 31/737* (2013.01); *A61K 41/0038* (2013.01); *A61N 5/1001* (2013.01); *A61N 5/1077* (2013.01); *A61N 5/1084* (2013.01); *A61N 2005/1024* (2013.01); *A61N 2005/1087* (2013.01); *A61N 2005/109* (2013.01); *A61N 2005/1091* (2013.01); *A61N 2005/1098* (2013.01)

(58) Field of Classification Search
CPC .............. A61K 2300/00; A61K 31/737; A61K 41/0038; A61K 41/00; A61N 2005/1024; A61N 2005/1087; A61N 2005/109; A61N 2005/1091; A61N 2005/1098; A61N 5/1001; A61N 5/1077; A61N 5/1084; A61N 5/10; A61N 5/103; A61P 35/00
See application file for complete search history.

(56) References Cited

U.S. PATENT DOCUMENTS

| | | | |
|---|---|---|---|
| 2,599,172 | A | 6/1952 | Hadidian |
| 4,240,163 | A | 12/1980 | Galin |
| 4,814,437 | A | 3/1989 | De Belder et al. |
| 4,851,521 | A | 7/1989 | Della Valle et al. |
| 5,008,253 | A | 4/1991 | Casu et al. |
| 5,166,331 | A | 11/1992 | Della Valle et al. |
| 5,442,053 | A | 8/1995 | Della Valle et al. |
| 5,559,104 | A | 9/1996 | Romeo et al. |
| 5,981,509 | A | 11/1999 | Akima et al. |
| 6,288,043 | B1 | 9/2001 | Spiro et al. |
| 6,339,074 | B1 | 1/2002 | Cialdi et al. |
| 6,803,037 | B2 | 10/2004 | Abatangelo et al. |
| 6,828,308 | B2 | 12/2004 | Mastradonato et al. |
| 6,833,363 | B2 | 12/2004 | Renier et al. |
| 7,202,230 | B2 | 4/2007 | Rivarossa et al. |
| 7,683,038 | B2 | 3/2010 | Bellini et al. |
| 7,855,187 | B1 | 12/2010 | Prestwich et al. |
| 8,329,673 | B2 | 12/2012 | Prestwich et al. |
| 8,343,942 | B2 | 1/2013 | Oottamasathien et al. |
| 8,399,430 | B2 | 3/2013 | Prestwich et al. |
| 8,951,990 | B2 | 2/2015 | Prestwich et al. |
| 11,173,325 | B2 * | 11/2021 | Parry ...................... A61K 9/51 |

(Continued)

FOREIGN PATENT DOCUMENTS

| | | |
|---|---|---|
| DE | 19813234 A1 | 9/1999 |
| DE | 102005004643 A1 | 8/2006 |

(Continued)

OTHER PUBLICATIONS

Jordan et al. Oncotarget, 2017, vol. 8, (No. 15), pp. 24262-24274. Antitumor activity of sulfated hyaluronic acid fragments in pre-clinical models of bladder cancer. (Year: 2017).*
International Search Report for PCT/US2019/060834 mailed Jan. 29, 2020.
Suzuki et al., "Preparation and inhibitory activity on hyaluronidase of fully O-sulfated hyaluro-oligosaccharides," Glycobiol., 2001, 11:57-64.
Talman et al., "Ocular changes induced by polysaccharides. II. Detection of hyaluronic acid sulfate after injection into ocular tissues," Am. J. Ophthalmol., 1959, 47:428-437.

(Continued)

*Primary Examiner* — Aradhana Sasan
*Assistant Examiner* — Mercy H Sabila
(74) *Attorney, Agent, or Firm* — Thomas | Horstemeyer, LLP

(57) ABSTRACT

Described herein are methods for reducing or maintaining the size of a tumor in a subject, where the method involves exposing the tumor to ionizing radiation and administering to the subject a modified hyaluronan or a pharmaceutically acceptable salt or ester. The use of the modified hyaluronan enhances or potentiates the effect of ionizing radiation used in cancer treatment. Additionally, the methods described herein prevent or reduces tumor regrowth in the subject after exposing the tumor to ionizing radiation and administration of the modified hyaluronan to the subject.

12 Claims, 5 Drawing Sheets

(56) References Cited

U.S. PATENT DOCUMENTS

| | | | |
|---|---|---|---|
| 11,642,366 B2* | 5/2023 | Lee | A61P 39/00 514/56 |
| 2002/0049183 A1 | 4/2002 | Yedgar et al. | |
| 2003/0198599 A1 | 10/2003 | Yalpani | |
| 2003/0199687 A1 | 10/2003 | Yalpani | |
| 2004/0053885 A1 | 3/2004 | Venbrocks et al. | |
| 2005/0119219 A1 | 6/2005 | Bellini et al. | |
| 2005/0203056 A1 | 9/2005 | Ulmer et al. | |
| 2006/0083711 A1 | 4/2006 | Berry et al. | |
| 2006/0172967 A1 | 8/2006 | Toida | |
| 2006/0223781 A1 | 10/2006 | Guo et al. | |
| 2007/0054878 A1 | 3/2007 | Venbrocks et al. | |
| 2008/0025950 A1 | 1/2008 | Prestwich et al. | |
| 2008/0032920 A1 | 2/2008 | Prestwich et al. | |
| 2008/0050335 A1 | 2/2008 | Faour et al. | |
| 2008/0182982 A1 | 7/2008 | Kumar et al. | |
| 2008/0306022 A1 | 12/2008 | Miyamoto et al. | |
| 2008/0306023 A1 | 12/2008 | Rinaudo et al. | |
| 2009/0093429 A1 | 4/2009 | Fu et al. | |
| 2009/0105463 A1 | 4/2009 | Berry et al. | |
| 2009/0197807 A1 | 8/2009 | Callegaro et al. | |
| 2009/0202639 A1 | 8/2009 | Bellini et al. | |
| 2009/0009342 A1 | 9/2009 | Fu et al. | |
| 2009/0226499 A1 | 9/2009 | Wisniewski et al. | |
| 2009/0252810 A1 | 10/2009 | Tommeraas et al. | |
| 2009/0285850 A1 | 11/2009 | Dillon et al. | |
| 2010/0204325 A1 | 8/2010 | Blanda et al. | |
| 2010/0278877 A1 | 11/2010 | Tamura et al. | |
| 2010/0317616 A1 | 12/2010 | Prestwich et al. | |
| 2011/0082104 A1 | 4/2011 | Prestwich et al. | |
| 2012/0021968 A1 | 1/2012 | Oottamasathien et al. | |
| 2013/0035307 A1 | 2/2013 | Prestwich et al. | |
| 2013/0190234 A1 | 7/2013 | Prestwich et al. | |
| 2013/0209531 A1* | 8/2013 | Prestwich | A61K 8/735 424/56 |
| 2014/0343011 A1 | 11/2014 | Prestwich et al. | |
| 2015/0209385 A1* | 7/2015 | Prestwich | A61P 13/00 536/53 |

FOREIGN PATENT DOCUMENTS

| | | |
|---|---|---|
| EP | 0214879 A2 | 3/1987 |
| EP | 0244178 A2 | 11/1987 |
| EP | 0285357 A2 | 10/1988 |
| EP | 0601055 A1 | 6/1994 |
| EP | 0754460 A1 | 1/1997 |
| EP | 0889055 A1 | 1/1999 |
| EP | 0925310 A1 | 6/1999 |
| EP | 1022289 A1 | 7/2000 |
| EP | 1087797 A1 | 4/2001 |
| EP | 1144459 A2 | 10/2001 |
| EP | 1169387 A1 | 1/2002 |
| EP | 1365777 A2 | 12/2003 |
| EP | 1901786 A2 | 3/2008 |
| EP | 1994062 A1 | 11/2008 |
| FR | 2864090 A1 | 6/2005 |
| JP | H11269077 A | 10/1999 |
| JP | H11279042 A | 10/1999 |
| JP | 2001097997 A | 4/2001 |
| JP | 2001163789 A | 6/2001 |
| JP | 2011516672 A | 5/2011 |
| JP | 2013529598 A | 7/2013 |
| KR | 20140042795 A | 4/2014 |
| WO | 1989007932 A1 | 9/1989 |
| WO | 1999043728 A1 | 9/1999 |
| WO | WO2000059422 A1 * | 10/2000 |
| WO | 2004004744 A1 | 1/2004 |
| WO | 2005046562 A2 | 5/2005 |
| WO | 2005056608 A1 | 6/2005 |
| WO | 2007006403 A2 | 1/2007 |
| WO | 2007043050 A2 | 4/2007 |
| WO | 2008008859 A2 | 1/2008 |
| WO | 2009013162 A1 | 1/2009 |
| WO | 2009059748 A2 | 5/2009 |
| WO | 2009124266 A2 | 10/2009 |
| WO | 2010087207 A1 | 8/2010 |
| WO | 2010121700 A1 | 10/2010 |
| WO | 2010130466 A1 | 11/2010 |
| WO | 2010130468 A1 | 11/2010 |
| WO | 2011156445 A1 | 12/2011 |
| WO | 2018053111 A1 | 3/2018 |

OTHER PUBLICATIONS

Talman et al., "Ocular changes induced by polysaccharides. III. Paper chromatographic fractionation of a biologically active hyaluronic acid sulfate preparation," Am. J. Ophthalmol., 1959, 48:560-572.

Tan. BK, et al; Chronic rhinosinusitis: the unrecognized epidemic. Am J Respir Crit Care Med 2013; 188: 1275-1277.

Theoharides et al., "A pilot open label of CystoProtek in interstitial cystitis," Int. J. Immunopathol. Pharmacol., 2005, 18:183-188.

Theoharides, "Treatment approaches for painful bladder syndrome/interstitial cystitis," Drugs, 2007, 67:215-235.

Toft et al., "Recent developments of intravesical therapy of painful bladder syndrome/interstitial cystitis: a review," Curr. Opin. Urol., 2006, 16:268-272.

Tomassen, P, et al. Inflammatory endotypes of chronic rhinosinusitis based on cluster analysis of biomarkers. J Allergy Clin Immunol 2016; 137:1449-1456 e1444.

Turino, GM, et al; Hyaluronan in respiratory injury and repair. Am J Respir Crit Care Med 2003; 167:1169-1175.

Yamamoto et al., "Absorption of water-soluble compounds with different molecular weights and [Asu1.7]-eel calcitonin from various mucosal administration sites," J. Controlled Release, 2001, 76:363-374.

Yildiz-Pekoz, A, et al; Inhaled Heparin: Therapeutic Efficacy and Recent Formulations. J Aerosol Med Pulm Drug Deliv 2017; 30:143-156.

Zhang, J, et al; Novel sulfated polysaccharides disrupt cathelicidins, inhibit RAGE and reduce cutaneous inflammation in a mouse model of rosacea. PLoS One 2011; 6:el6658 (14 pp).

English translation of Korean Office Action for KR 10-2013-7027636 dated Mar. 21, 2018, 8pp.

European Search Report for European application No. 1179068.5 dated Jul. 10, 2013.

Extended European Search Report for European Application No. 12761460.0 dated Aug. 27, 2014.

International Search Report and Written Opinion for PCT/US18/56419 dated Dec. 11, 2018 (12pp).

International Search Report for PCT/US09/39498 dated Oct. 29, 2009.

International Search Report for PCT/US11/39550 dated Sep. 29, 2011.

International Search Report for PCT/US12/30233 dated Jul. 3, 2012.

IPRP for PCT/US09/39498 dated Dec. 8, 2010.

Israeli Office Action for Patent Application No. 228605 dated May 1, 2016 (translation, 2 pp).

Office Action for JP 2013-514324 dated Apr. 24, 2015 (English translation, 5 pp).

Office Action for JP 2015-253460 dated Sep. 21, 2016 (English translation, 13 pp).

US Office Action for U.S. Appl. No. 12/870,763 dated Sep. 17, 2010.

US Office Action for U.S. Appl. No. 12/870,774 dated Jul. 17, 2012.

US Office Action for U.S. Appl. No. 12/870,774 dated Mar. 5, 2012.

US Office Action for U.S. Appl. No. 13/069,860 dated Mar. 29, 2012.

US Office Action for U.S. Appl. No. 13/304,292 dated Feb. 21, 2012.

US Office Action for 15/381, 187 dated Apr. 4, 2018, 10pp.

Written opinion of the ISA for PCT/US09/39498 dated Apr. 10, 2010.

Theoharides et al., "Critical role of mast cells in inflammatory diseases and the effect of acute stress," J. Neuroimmunol., 2004, 146:1-12.

Simon et al., Allergy, 2004;59:561-570.

(56) References Cited

OTHER PUBLICATIONS

Yang et al., BioDrugs, 2021;35(4):401-415YANG et al., BioDrugs, 2021;35(4):401-415.
Brandt et al., J Clin Cell Immunol, 2011;2(3):110.
Chinese Office Action for Chinese Patent Application No. 201910048776.3 mailed Dec. 11, 2023.
Lindsay, R, et al; Development of a murine model of chronic rhinosinusitis. Otolaryngol Head Neck Surg 2006; 134:724-730; discussion 731-722.
Liu, T, et al.; A possible association of *Staphylococcus* enterotoxin B-induced asthma and sinusitis. J Huazhong Univ Sci Technolog Med Sci 2006; 26:63-67 (abstract only).
Lukban et al., "Current management of interstitial cystitis," Urol. Clin. N. Am., 2002, 29:649-660.
Macrae et al., "The effects of sodium hyaluronate, chondroitin sulfate, and methyl cellulose on the corneal endothelium and intraocular pressure," Am. J. Ophthalmol., 1983, 95:332-41.
Magnani, A. et al., "Blood-interaction performance of differently sulphated hyaluronic acids," 1996, Thrombosis Research, 81:383-395.
Manzanares, D, et al; Apical oxidative hyaluronan degradation stimulates airway ciliary beating via RHAMM and RON. Am J Respir Cell Mol Biol 2007; 37:160-168.
Maruyama et al., "Conformational changes and anticoagulant activity of chondroitin sulfate following its O-sulfonation," Carb. Res., 1998, 306:35-43.
Matsuda, M. et al. "Therapeutic effect of sulphated hyaluronic acid, a potential selectin-blocing agent, on experimental progressive mesangial proliferative glomerulonephritis," J. Pathol., 2002, 198:407-414.
Mracek et al., "The Diffusion Process of Sodium Hyaluronate (Na-HA) and Na-HA-n-alkyl Derivatives Films Swelling," J. Biomed. Mater. Res. Part A, 2007, 83A/1:184-190.
Myint et al., "RAGE Control of Diabetic Nephropathy in a Mouse Model: Effects of RAGE Gene Disruption and Administration of Low-Molecular Weight Heparin," Diabetes, 2006, 55:2510-2522.
Nagasawa et al., "Chemical sulfation of preparations of chondroitin 4- and 6-sulfate, and dermatan sulfate. Preparation of chondroitin sulfate like materials from chondroitin 4-sulfate," Carb. Res., 1986, 158:183-190.
Nagira et al., "Effects of sulfated hyaluronin on keratinocyte differentiation and Wnt and Notch gene expression," Biomaterials, 2007, 2:844-850.
Nakagawa, T, et al; Comparative assessment of cell proliferation and accumulation of extracellular matrix in nasal polyps. Acta Otolaryngol Suppl 1998; 538:205-208.
Nakamura et al., "Concentration and molecular weight dependency of rabbit corneal epithelial wound healing on hyaluronan," Curr. Eye Res., 1992, 11:981-986.
Nepp et al., "The clinical use of viscoelastic artificial tears and sodium chloride in dry-eye syndrome," Biomaterials, 2001, 22:3305-3310.
Ogawa, D. et al. "Sulfated Hyaluronic Acid, a Potential Selectin Inhibitor, Ameliorates Experimentally Induced Crescentic Glomerulonephritis," Experimental Nephrology, 2005, 99:e26-e32.
Oottamasathien, S, et al; A murine model of inflammatory bladder disease: cathelicidin peptide induced bladder inflammation and treatment with sulfated polysaccharides. J Urol 2011; 186: 1684-1692.
Orlandi, RR, et al; International Consensus Statement on Allergy and Rhinology: Rhinosinusitis Executive Summary. International forum of allergy & rhinology 2016; 6 Suppl I:S3-21.
Orlandi, RR, et al; International Consensus Statement on Allergy and Rhinology: Rhinosinusitis. Int Forum Allergy Rhinol 2016; 6 Suppl 1:S22-209.
Pakdaman, MN, et al; Fungi linking the pathophysiology of chronic rhinosinusitis with nasal polyps and allergic asthma. Immunol Invest 2011; 40:767-785 (abstract only).
Pant, H, et al; CD4(+) and CDS(+) regulatory T cells in chronic rhinosinusitis mucosa. Am J Rhinol Allergy 2014; 28: e83-89.
Parsons et al., "Treatment of interstitial cystitis with intravesical heparin," Br. J. Urol., 1994, 73:504-507.
Parsons, "Successful downregulation of bladder sensory nerves with combination of heparin and alkalinized lidocaine in patients with interstitial cystitis," Urology, 2005, 74:45-48.
Payne et al., "Interstitial cystitis and painful bladder syndrome," J. Urol., 2007, 177:2042-9.
Petit et al., "Controlled sulfonation of natural anionic bacterial polysaccharides can yield agents with specific regenerating activity in vivo," Biomacromolecules, 2004, 5:445-452.
Pulsipher, A, et al; Prevention of sinonasal inflammation by a synthetic glycosaminoglycan. Int Forum Allergy Rhinol 2017; 7: 177-184.
Rao, NV, et al; Low anticoagulant heparin targets multiple sites of inflammation, suppresses heparin-induced thrombocytopenia, and inhibits interaction of RAGE with its ligands. Am J Physiol Cell Physiol 2010; 299:C97-110.
Romano, CL et al; "Hyaluronic acid and its composites as a local antimicrobial/antiadhesive barrier," J. Bone and Joint Infection; 2017, 2:63-72.
Rudmik, L, et al; Impact of topical nasal steroid therapy on symptoms of nasal polyposis: a meta-analysis. Laryngoscope 2012; 122:1431-1437.
Rudmik, L, et al; Topical therapies in the management of chronic rhinosinusitis: an evidence-based review with recommendations. Int Forum Allergy Rhinol 2013; 3:281-298.
Rudmik, L; Chronic rhinosinusitis: an under-researched epidemic. J Otolaryngol Head Neck Surg 2015; 44:11.
Saary, J. et al., "A systematic review of contact dermatitis treatment and prevention," 2005, J. Am. Acad. Dermatol., 53:845-855 and 845e1-845e13.
Sant et al., "A pilot clinical trial of oral pentosan polysulfate and oral hydroxyzine in patients with interstitial cystitis," J. Urol., 2003, 170:810-815.
Satoh et al., "The Basic Research on Physiological Property of Functionalized Hyaluronan (II): Effect of Sulfated Hyaluronan on Histamine Release from the Mast Cell," Fiber, 2004, 60:137-143.
Satoh et al., "The research on physiological property of functionalized hyaluronan: interaction between sulfated hyaluronan and plasma proteins," Polymers for Advanced Technologies, 2004, 15:720-725.
Savage, Jr, et al; A Modified Glycosarninoglycan, GM-0111, Inhibits Molecular Signaling Involved in Periodontitis. PLoS One 2016; II:e0157310 (20 pp).
SBIR Award ID:93482. "Sulfated Polysaccharide Derivatives for the Treatment of Rosacea," Glycomira, 2009, Abstract only. <http://www.sbir.gov/sbiresearch/detail/192860>, accessed Jun. 27, 2014.
SBIR Award ID:93781. "Sulfated Polysaccharide Derivatives for the Treatment of Macular Degeneration," Glycomira, 2009, Abstract only. <http://www.sbir.gov/sbiresearch/detail/192862>, accessed Jun. 27, 2014.
Schleimer, RP; Immunopathogenesis of Chronic Rhinosinusitis and Nasal Polyposis. Annu Rev Pathol 2017; 12:331-357.
Schlosser, RJ, et al; Burden of illness: A systematic review of depression in chronic rhinosinusitis. Am J Rhinol Allergy 2016; 30:250-256.
Schuh, JM, et al; An inhalation model of allergic fungal asthma: Aspergillus furnigatus-induced inflammation and remodeling in allergic airway disease. Methods Mol Biol 2013; 1032:173-184.
Schwartz, JS, et al; Medical management of chronic rhinosinusitis—an update. Expert Rev Clin Pharmacol 2016; 9:695-704 (abstract only).
Smith, KA, et al; Medical therapy, refractory chronic rhinosinusitis, and productivity costs. Curr Opin Allergy Clin Immunol 2017; 17:5-11 (abstract only).
Snidvongs, K, et al; Update on Intranasal Medications in Rhinosinusitis. Curr Allergy Asthma Rep 2017; 17:47 (abstract only).
Soler, ZM, et al; Health state utility values in patients undergoing endoscopic sinus surgery. Laryngoscope 2011; 121:2672-2678.
Souza-Fernandes, AB, et al; Bench-to-bedside review: the role of glycosaminoglycans in respiratory disease. Crit Care 2006; 10:237 (16 pp).
Steinhoff et al., "The efficacy of chondroitin sulfate 0.2% in treating interstitial cystitis," Can. J. Urol., 2002, 9:1454-1458.

(56) References Cited

OTHER PUBLICATIONS

Stevens, WW, et al; Chronic rhinosinusitis pathogenesis. J Allergy Clin Immunol 2015; 136:1442-1453.
Sun, Y, et al; Biofilm formation and Toll-like receptor 2, Tol••like receptor 4, and NF-kappaB expression in sinus tissues of patients with chronic rhinosinusitis. Am J Rhinol Allergy 2012; 26: 104-109.
Sasaki, Takehito. "Biological Basis for Chemoradiation Therapy—A Review." The Journal of JASTRO 10, No. 3 (1998): 195-204.
Akimoto, Tetsuo. "Currently Perspectives of Radiation Therapy Chemotherapy and Molecular Target Therapy Combined with Radiation Therapy." Radioisotopes, 61 21-29 (2012).
Japanese Office Action for Japanese Patent Application No. 2021-525704 mailed Nov. 9, 2023.
Korean Office Action for Korean Patent Application No. 520210373464 mailed Sep. 21, 2023.
Abbadi, A, et al; Hyaluronan Rafts on Airway Epithelial Cells. J Biol Chem 2016; 291:1448-1455.
Abtangelo et al., "Biocompatibility and enzymatic degradation studies on sulphated hyaluronic acid derivatives," Biomaterials, 1997, 18:1411-1415.
Allmen et al., "V domain of RAGE interacts with AGEs on prostate carcinoma cells," The Prostate, 2008, 68:748-758.
Al-Mutairi, D, et al; Bacterial biofilms and the pathophysiology of chronic rhinosinusitis. Curr Opin Allergy Clin Immunol 2011; 11: 18-23 (abstract only).
Alt, JA, et al; Predictors of olfactory dysfunction in rhinosinusitis using the brief smell identification test. Laryngoscope 2014, 124:E259-E266.
Alt, JA, et al; Quality of Life in Patients With Chronic Rhinosinusitis and Sleep Dysfunction Undergoing Endoscopic Sinus Surgery: A Pilot Investigation of Comorbid Obstructive Sleep Apnea. JAMA Otolaryngology—Head & Neck Surgery 2015, 141:1-9.
Anderson et al., "Pentosan polysulfate: a review of its use in the relief of bladder pain or discomfort in interstitial cystitis," Drugs, 2006, 66:821-835.
Baba, S, et al; Distribution, subtype population, and IgE positivity of mast cells in chronic rhinosinusitis with nasal polyps. Ann Allergy Asthma Immunol 2017, 119:120-128.
Bachert, C, et al; Biotherapeutics in Chronic Rhinosinusitis with and without Nasal Polyps. J Allergy Clin Immunol Pract 2017, 5:1512-1516.
Bachert, C, et al; ICON: chronic rhinosinusitis. World Allergy Organ J 2014; 7:25 (28pp).
Barbucci, "Low- and high-resolution nuclear magnetic resonance (NMR) characterisation of hyaluronan-based native and sulfated hydrogels," Carbohydrate Res., 2006, 341:1848-1858.
Baykal et al., "Intravesical heparin and peripheral neuromodulation on interstitial cystitis," Urol. Int., 2005, 74:361-364.
Benck et al., "Proteinuria-lowering effect of heparin therapy in diabetic nephropathy without affecting the renin-angiotensin-aldosterone system," Clin. J. Am. Soc. Nephrol., 2007, 2:58-67.
Benesova et al., "Satbility evaluation of n-alkyl hyaluronic acid derivatives by DSC and TG measurement," J. Therm. Analys. Calorim., 2006, 83:341-348.
Benitez et al., "Targeting hyaluronidase for cancer therapy: antitumor activity of sulfated hyaluronic acid in prostate cancer cells," Canc. Res., 2011, 71:4085-4095.
Bhattacharyya, N; Ambulatory sinus and nasal surgery in the United States: demographics and perioperative outcomes. Laryngoscope 2010; 120:635-638.
Bhattacharyya, N; Functional limitations and workdays lost associated with chronic rhinosinusitis and allergic rhinitis. Am J Rhinol Allergy 2012; 26: 120-122.
Bhattacharyya, N; Incremental health care utilization and expenditures for chronic rhinosinusitis in the United States. Ann Otol Rhinol Laryngol 2011; 120:423-427.
Bohlender et al., "Advanced glycation end products in the kidney," Am. J. Renal. Physiol., 2005, 289:F645-F659.
Caulley, L, et al; Direct costs of adult chronic rhinosinusitis by using 4 methods of estimation: Results of the US Medical Expenditure Panel Survey. J Allergy Clin Immunol 2015; 136: 1517-1522.
Cen et al., "Assessment of in vitro Bioactivity of Hyaluronic Acid and Sulfated Hyaluronic Acid Functionalized Electroactive Polymer," Biomacromolecules, 2004, 5:2238-2246.
Cheng et al., "Expression profiling of endogenous secretory receptor for advanced glycation end products in human organs," Modern Pathol., 2005, 18:1385-1396.
Dausse et al., "Cartilage Repair Using New Polysaccharidic Biomaterials: Macroscopic, Histological and Biochemical Approaches in a Rat Model of Cartilage Defect," Osteoarthritis and Cartilage, 2003, 11:16-28.
Deconde, AS, et al.; Chronic rhinosinusitis: Epidemiology and burden of disease. Am J Rhinol Allergy 2016; 30:134-139.
Derycke, L, et al; Mixed T helper cell signatures in chronic rhinosinusitis with and without polyps. PLoS One 2014; 9: e97581 (8 pp).
Hamilos, DL.; Chronic rhinosinusitis: epidemiology and medical management. J Allergy Clin Immunol 2011; 128:693-707; quiz 708-699.
Hammer, "Viscous corneal protection by sodium hyaluronate, chondroitin sulfate, and methylcellulose," Invest. Ophthalmol. Vis. Sci., 1984, 25:1329-1332.
Hermani et al., "Calcium-binding proteins S100A8 and S100A9 as Novel Diagnostic Markers in Human Prostate Cancer," Clin. Cancer Res., 2005, 11:5146-5152.
Hintze et al., "Modifications of hyaluronan influence the interaction with human bone morphogenetic protein-4 (hBMP-4)," Biomacromolecules, 2009, 10:3290:3297.
Iavazzo et al., "Hyaluronic acid: an effective alternative treatment of interstitial cystitis, recurrent urinary tract infections, and hemorrhagic cystitis?" Europ. Urol., 2007, 51:1534-1541.
Ishiguro et al., "Receptor for advanced glycation end products (RAGE) and its ligand, amphoterin, are overexpressed and associated with prostate cancer development," The Prostate, 2005, 64:92-100.
Jacob, A, et al; Survey anatomy of the paranasal sinuses in the normal mouse. Laryngoscope 2006; 116:558-563.
Jeanloz, "The methyl ester of methylated hyaluronic acid," J. Biol. Chem., 1952, 197:141-150.
Jia, M, et al; A simple animal model of *Staphylococcus aureus* biofilm in sinusitis. Am J Rhinol Allergy 2014; 28:e115-e119.
Johnson, Z, et al; Interaction of chemokines and glycosaminoglycans: a new twist in the regulation of chemokine function with opportunities for therapeutic intervention. Cytokine Growth Factor Rev 2005; 16:625-636.
Jones et al., "Epidemiology of interstitial cystitis," Urology, 1997, 49 (5A Suppl.):2-9.
Jouy, F, et al., "Sulfated hyaluronan attenuates inflammatory signaling pathways in macrophages involving induction of antioxidants," Proteomics, 2017, 17:170082 (11pp).
Jura-Szoltys, E, et al; Epistaxis as the reason for premature discontinuation of clopidogrel after percutaneous coronary angioplasty with stent implantation. Kardiol Pol 2011; 69:817-823 (abstract only).
Kaye et al., "Methylation studies on hyaluronic acid," Biochem. J., 1951, 48:249.
Kennedy, JL, et al; Chronic sinusitis pathophysiology: the role of allergy. Am J Rhinol Allergy 2013; 27:367-371.
Kilty, SJ, et al; The role of bacterial biofilms and the pathophysiology of chronic rhinosinusitis. Curr Allergy Asthma Rep 2008; 8:227-233.
Kyyronen, "Methylprednisolone esters of hyaluronic acid in ophthalmic drug delivery: in vitro and in vivo release studies," Int. J. Pharmaceutics, 1992, 80:161-169.
Ledson, M, et al; Nebulized heparin in Burkholderia cepacia colonized adult cystic fibrosis patients. Eur Respir J 2001; 17:36-38.
Lee, S, et al; Chronic rhinosinusitis as a multifactorial inflammatory disorder. Curr Infect Dis Rep 2011; 13: 15 9-168.
Liang, J, et al; Topical Drug Delivery for Chronic Rhinosinusitis. Curr Otorhinolaryngol Rep 2013; 1 : 51-60.

(56) References Cited

OTHER PUBLICATIONS

Limberg et al., "Topical application of hyaluronic acid and chondroitin sulfate in the treatment of dry eyes," Am. J. Ophthalmol., 1987, 103:194-197.
Examination Report for AU Application No. 2019380363 mailed Jul. 8, 2024.

* cited by examiner

Group 3: Sham + PBS

Group 4: Sham + GM-1111

Group 5: 2Gy x 5 + PBS

Group 6: 2Gy x 5 + GM-1111

METHODS FOR POTENTIATING CANCER TREATMENT USING IONIZING RADIATION

CROSS REFERENCE TO RELATED APPLICATIONS

This application claims priority upon U.S. provisional application Ser. No. 62/760,134, filed Nov. 13, 2018. This application is hereby incorporated by reference in its entirety.

ACKNOWLEDGMENTS

This invention was made with government support under Grant No. 2R44DE024024 awarded by the National Institute of Dental and Craniofacial Research. The government has certain rights in the invention.

BACKGROUND

Used with surgery, radiation therapy is a powerful tool to induce tumor regression. However, many types of cancers eventually develop resistance to the radiation and the radiation therapy becomes ineffective [1-6]. In addition, irradiation-induced damages in healthy tissues cause acute and chronic diseases such as radiation burns in the skin, pneumonitis, and oral mucositis that can complicate the tolerance to the radiation therapy. To reduce radiation-induced damage to healthy tissue, irradiation is usually done in multiple smaller doses. Nevertheless, these fractionated irradiation strategies still cause damage to the exposed tissues and organs. Because of these drawbacks, there is a growing interest in radiation sensitizers that enhance the effectiveness of radiation and reduce side effects. Various types of radiation sensitizers such as chemotherapeutic agents, adjuvants, and modified formulations have been steadily employed over the years [7-9]. Currently, chemotherapeutic agents such as 5-FU and cisplatin are commonly used as radiation sensitizers. While these radiation sensitizers can enhance the efficacy of cancer therapy, most of these chemotherapeutic agents also cause a diverse array of adverse health consequences. Mucosal tissues such as oral and gastrointestinal mucosa are highly sensitive to chemoradiation and patients frequently develop seriously painful oral and intestinal mucositis. The severity of these chemoradiation-induced diseases can be a limiting factor for cancer treatments and the lack of proper intervention can lead to debilitating chronic illnesses. Development of a radiation sensitizing agent without serious side effects would improve the overall success of cancer therapy.

SUMMARY

Described herein are methods for reducing or maintaining the size of a tumor in a subject, where the method involves exposing the tumor to ionizing radiation and administering to the subject a modified hyaluronan or a pharmaceutically acceptable salt or ester. The use of the modified hyaluronan enhances or potentiates the effect of ionizing radiation used in cancer treatment. Additionally, the methods described herein prevent or reduces tumor regrowth in the subject after exposing the tumor to ionizing radiation and administration of the modified hyaluronan to the subject.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
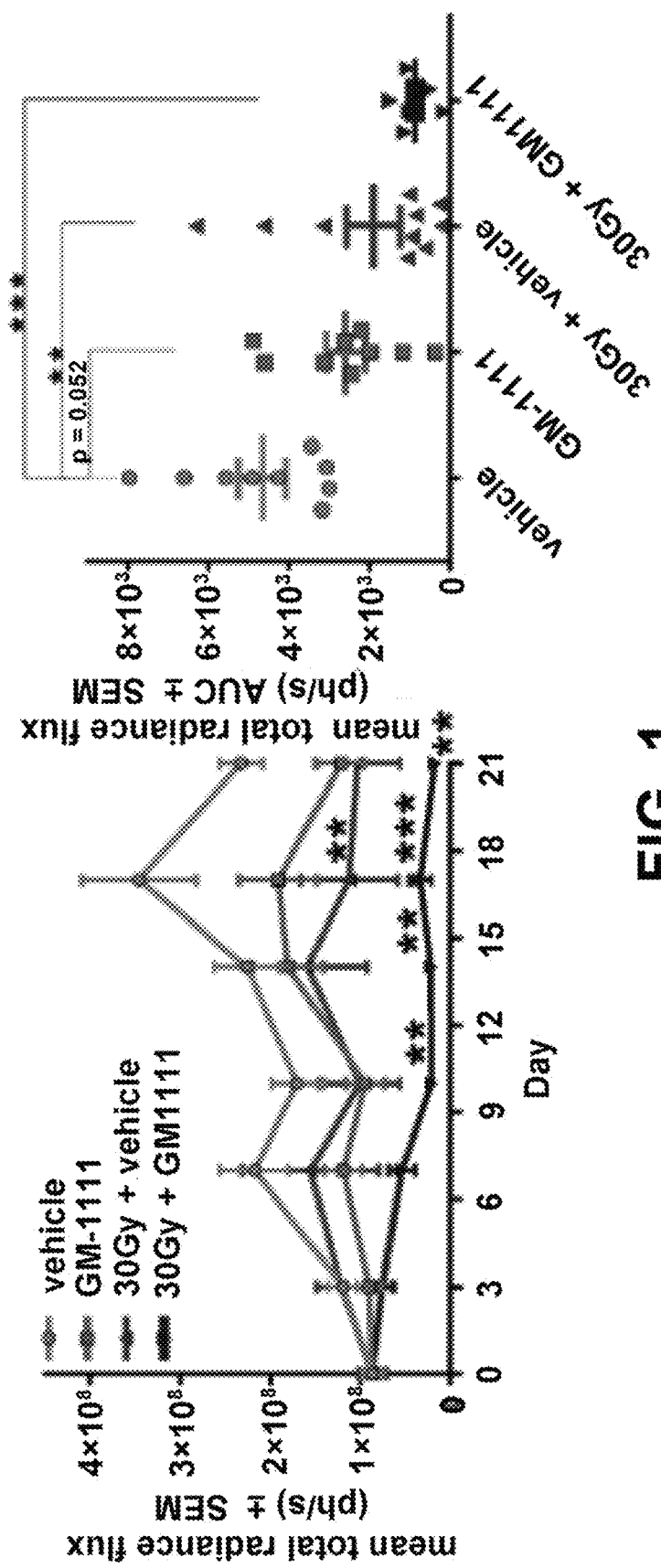
FIG. 1 shows the growth of the established tumor. Tumor volume was determined by measuring the luminescence from the implanted SCC-25-Luc2 cells. Two groups of animals were irradiated with x-rays (30 Gy) once on day 0. Both GM-1111 (30 mg/kg) and vehicle (phosphate buffered saline, PBS) were administered subcutaneously once daily from day 1 to day 20. Left panel illustrates the changes of tumor volume over time and right panel shows the area under the curve (tumor volume vs. day curve) for each group. Symbols and error bars represent mean±SEM. $p<0.01$ and *$p<0.001$ compared to Vehicle treatment group.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

As used herein, a plurality of items, structural elements, compositional elements, and/or materials may be presented in a common list for convenience. However, these lists should be construed as though each member of the list is individually identified as a separate and unique member. Thus, no individual member of any such list should be construed as a de facto equivalent of any other member of the same list based solely on its presentation in a common group, without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an example, a numerical range of "about 1" to "about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, from about 1-about 3, from 1 to about 3, from about 1 to 3, etc., as well as 1, 2, 3, 4, and 5, individually. The same principle applies to ranges reciting only one numerical value as a minimum or maximum. Furthermore, such an interpretation should apply regardless of the breadth or range of the characters being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference of each various individual and collective combination and permutation of these compounds may not be explicitly disclosed, each is specifically contemplated and described herein. For example, if a class of molecules A, B, and C are disclosed, as well as a class of molecules D, E, and F, and an example of a combination A+D is disclosed, then even if each is not individually recited, each is individually and collectively contemplated. Thus, in this example, each of the combinations A+E, A+F, B+D, B+E, B+F, =C+D, C+E, and C+F, are specifically contemplated and should be considered disclosed from disclosure of A, B, and C; D, E, and F; and the example combination of A+D. Likewise, any subset or combination of these is also specifically contemplated and disclosed. Thus, for example, the sub-group of A+E, B+F, and C+E is specifically contemplated and should be considered disclosed from disclosure of A, B, and C; D, E, and F; and the example combination of A+D. This concept applies to all aspects of this disclosure including, but not limited to, steps in methods of making and using the disclosed compositions. Thus, if there exist a variety of additional steps that can be performed with any specific embodiment or combination of embodiments of the disclosed methods, each such combination is specifically contemplated and should be considered disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, hyaluronan that contains at least one —OH group can be represented by the formula Y—OH, where Y is the remainder (i.e., residue) of the hyaluronan molecule.

The term "treat" as used herein is defined as maintaining or reducing the symptoms of a pre-existing condition (e.g., tumor volume) using the methods described herein when compared to the same condition in the absence of using the methods described herein. The term "prevent" as used herein is defined as eliminating or reducing the likelihood of the occurrence of one or more symptoms (e.g., tumor growth, tumor regrowth, etc.) using the methods described herein when compared to the same symptom in the absence of using the methods described herein. The term "inhibit" as used herein is the ability of the methods described herein to completely eliminate the activity or reduce the activity (e.g., tumor growth, tumor regrowth, etc.) when compared to the same activity in the absence of using the methods described herein.

"Subject" refers to mammals including, but not limited to, humans, non-human primates, sheep, dogs, rodents (e.g., mouse, rat, etc.), guinea pigs, cats, rabbits, cows, and non-mammals including chickens, amphibians, and reptiles.

Described herein are methods for reducing or maintaining the size of a tumor in a subject with the use of ionizing radiation and a modified hyaluronan as described herein. The method involves exposing the tumor to ionizing radiation and administering to the subject a modified hyaluronan or a pharmaceutically acceptable salt or ester, wherein the modified hyaluronan or its pharmaceutically acceptable salt or ester comprises (a) a sulfated hyaluronan or the pharmaceutically acceptable salt or ester thereof or (b) hyaluronan comprising at least one sulfate group and at least one primary C-6 hydroxyl position of an N-acetyl-glucosamine residue comprising an alkyl group or fluoroalkyl group.

The use of the modified hyaluronan in combination with ionizing radiation has several unexpected properties with respect to treating tumors in cancer patients. As will be shown herein, tumor size and volume decreases significantly when the tumor is exposed to ionizing radiation and the subject is administered the modified hyaluronan compared to the size of the tumor that has only been exposed to ionizing radiation. Techniques known in the art can be used to measure the size (e.g., volume) of a tumor. Thus, the modified hyaluronan enhances the chemotherapeutic effect of the ionizing radiation. This is unexpected as the use of anti-inflammatory or cytoprotective drugs during cancer treatment can protect cancer tissues from the cytotoxic effects of chemoradiation.

Another advantage of the methods described herein is that they can prevent or reduce tumor regrowth in the subject when compared to the initial volume of the tumor prior to application of ionizing radiation and administration of modified hyaluronan. Many types of cancers eventually develop resistance to the radiation and the radiation therapy becomes ineffective. The methods described herein can prevent or reduce the likelihood of tumor resistance to ionizing energy or tumor regrowth.

The ionizing radiation useful herein is any radiation that can be applied to a tumor in a cancer patient. The term "ionizing radiation" as used herein is defined radiation that has sufficient energy to eject one or more orbital electrons from an atom or molecule (e.g., alpha particles, beta particles, gamma rays, x-rays, neutrons, protons, and other particles having sufficient energy to produce ion pairs in matter. Absorbed doses are typically measured in "grays" (Gy).

In one aspect, the ionizing radiation is external beam radiation, brachytherapy radiation, or a combination thereof. In one aspect, the external beam radiation includes radiation delivered from an ortho-voltage X-ray machine, a Cobalt-60 machine, a linear accelerator, a proton beam machine, a betatron radiation, a neutron beam machine, a gamma knife, spray radiation, stereotactic radiation, or any combination thereof. In another aspect, the brachytherapy radiation includes interstitial radiation, intracavitary radiation, intraluminal radiation, radioligand tagged molecules administered intravenously, or any combination thereof.

The amount and duration of the ionizing radiation can vary depending upon the size and nature of the tumor. The ionizing radiation can be applied in a single dose or multiple doses over time. In one aspect, the tumor is exposed to x-ray irradiation at a dosage of from 0.5 to 100 Gy, or 0.5, 1, 2, 2.5, 5, 10, 15, 20, 25, 30, 35, 40, 45, 50, 55, 60, 65, 70, 75, 80, 85, 90, 95, 100 Gy, where any value can be a lower and upper end-point of a range (e.g., 20 to 40 Gy).

The administration of the modified hyaluronan relative to the timing of the application of ionizing radiation can vary. In one aspect, the modified hyaluronan is administered to the subject after the tumor is exposed to ionizing radiation. In another aspect, the modified hyaluronan is administered to the subject before the tumor is exposed to ionizing radiation. In another aspect, the modified hyaluronan is administered to the subject before and after the tumor is exposed to ionizing radiation. In another aspect, the modified hyaluronan is administered to the subject while the tumor is exposed to ionizing radiation. In another aspect, the modified hyaluronan is administered to the subject while the tumor is exposed to ionizing radiation and administered subsequently after the tumor is exposed to ionizing radiation.

In one aspect, the modified hyaluronan is administered to the subject within 0.5 hours to 72 hours after the initial exposure of the tumor to ionizing radiation. In another aspect, the modified hyaluronan is initially administered to the subject 0.5 hours, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 30 hours, 36 hours, 42 hours, 48 hours, 60 hours, or 72 hours after exposing the tumor to ionizing radiation, where any value can be a lower and upper-endpoint of a range (e.g., 12 hours to 24 hours).

The modified hyaluronan or the pharmaceutically acceptable salt or ester thereof can be administered once a day or multiple times per day (e.g., 2×, 4×, 8× daily or every other day) after the tumor has been exposed to ionizing radiation. The modified hyaluronan can be administered over a period of time depending upon the size of the tumor and amount of ionizing radiation. In one aspect, the modified hyaluronan or the pharmaceutically acceptable salt or ester thereof is administered to the subject daily for up to 28 days after exposing the tumor to ionizing radiation. In another aspect, the modified hyaluronan or a pharmaceutically acceptable salt or ester thereof is administered to the subject daily or every other day for 2 days, 3 days, 4 days, 5 days, 6 days, 7 days, 8 days, 9 days, 10 days, 12 days, 14 days, 16 days, 18 days, 20 days, 22, days, 24 days, 26 days, or 28 days after exposing the tumor to ionizing radiation, where any value can be a lower and upper-endpoint of a range (e.g., 2 days to 8 days).

In one aspect, the modified hyaluronan is a sulfated hyaluronan or the pharmaceutically acceptable salt or ester thereof. In one aspect, the sulfated hyaluronan has a degree of sulfation from 0.1 to 4.0 per disaccharide unit. In another aspect, the sulfated hyaluronan has a degree of sulfation from 0.1, 0.5, 1.0, 1.5, 2.0, 2.5, 3.0, 3.1, 3.2, 3.3, 3.4, 3.5, 3.6, 3.7, 3.8, 3.9, or 4.0 per disaccharide unit, where any value can be a lower and upper end-point of a range (e.g., 3.0 to 4.0, 3.2 to 3.8, etc.).

In another aspect, the average molecular weight of the sulfated hyaluronan is less than 1,000 kDa, less than 900 kDa, less than 800 kDa, less than 700 kDa, less than 600 kDa, less than 500 kDa, less than 400 kDa, less than 300 kDa, less than 200 kDa, less than 100 kDa, less than 50 kDa, less than 25 kDa, less than 10 kDa, or less than 5 kDa. In another aspect, the sulfated hyaluronan has an average molecular size from 0.5 kDa to less than 50 kDa, 2 Da to 20 kDa, or 3 kDa to 10 kDa. In a further aspect, the sulfated hyaluronan has an average molecular size from 0.5 kDa to 10 kDa or 1 kDa to 10 kDa. Depending upon reaction conditions, one or more different hydroxyl groups present in the low molecular hyaluronan or hyaluronan oligosaccharide can be sulfated. In one aspect, the primary C-6 hydroxyl proton of the N-acetyl-glucosamine residue of the low molecular hyaluronan or hyaluronan oligosaccharide is sulfated. In another aspect, the primary C-6 hydroxyl proton of the N-acetyl-glucosamine residue of hyaluronan and at least one C-2 hydroxyl proton or C-3 hydroxyl proton of a uronic acid residue or at least one C-4 hydroxyl proton of an N-acetyl-glucosamine residue is substituted with a sulfate group. In another aspect, the primary C-6 hydroxyl proton of the N-acetyl-glucosamine residue of the low molecular hyaluronan or hyaluronan oligosaccharide and at least one C-2 hydroxyl proton and C-3 hydroxyl proton of a uronic acid residue and at least one C-4 hydroxyl proton of an N-acetyl-glucosamine residue is substituted with a sulfate group. In another aspect, 0.001%, 0.01%, 0.1%, 1%, 5%, 10%, 20%, 30%, 40%, 50%, 60%, 70%, 80%, 90%, 95%, or less than 100%, or any range thereof of hydroxyl protons present on the low molecular hyaluronan or hyaluronan oligosaccharide can be deprotonated and subsequently sulfated.

In another aspect, the sulfated hyaluronan has (1) 90% of the primary C-6 hydroxyl protons of the N-acetyl-glucosamine residue of the sulfated hyaluronan are substituted with a sulfate group, (2) a degree of sulfation from 3.0 to 4.0, and (3) an average molecular weight from 1 kDa to 10 kDa. In another aspect, sulfated hyaluronan has (1) 100% of the primary C-6 hydroxyl protons of the N-acetyl-glucosamine residue of the sulfated hyaluronan are substituted with a sulfate group, (2) a degree of sulfation from 3.0 to 4.0, and (3) an average molecular weight from 1 kDa to 10 kDa.

The hyaluronan starting material used to produce the sulfated hyaluronan can exist as the free acid or the salt thereof. Derivatives of hyaluronan starting material can also be used herein. The derivatives include any modification of the hyaluronan prior to and/or after sulfation. A wide variety of molecular weight hyaluronans can be used herein for the depolymerization step. In one aspect, the hyaluronan has a molecular weight greater than 1,000 kDa prior to depolymerization. In another aspect, the hyaluronan can have a molecular weight of 10 kDa to 1,000 kDa prior to depolymerization. A wide variety of hyaluronan molecular weights can also be employed for the sulfation step. In one aspect, the hyaluronan starting material can be converted to low molecular hyaluronan or a hyaluronan oligosaccharide prior to sulfation to produce the partially or fully sulfated hyaluronan. As will be discussed in greater detail below, low molecular weight hyaluronan is hyaluronan that has been degraded with an acid or base or depolymerized by techniques known in the art including, but not limited to, ultrasound, ozonolysis, sheer stress, or radical-mediated chain cleavage. Alternatively, hyaluronan oligosaccharide is produced by degrading hyaluronan with an enzyme such as, for example, hyaluronan synthase or hyaluronidase in a controlled fashion. Subsequently, hyaluronan oligosaccharides having different molecular weights can be separated by GPC or ion exchange separation. Exemplary procedures for producing low molecular weight hyaluronan or hyaluronan oligosaccharide from hyaluronan are provided in WO 2011/156445.

In one aspect, the low molecular hyaluronan or hyaluronan oligosaccharide being sulfated has a molecular weight from 1 kDa to 2,000 kDa. In another aspect, the low molecular hyaluronan or hyaluronan oligosaccharide being sulfated has a molecular weight from 5 kDa to 500 kDa, 10 kDa to 200 kDa, or 20 kDa to 100 kDa, or less than 200 kDa, 150 kDa, 100 kDa, 75 kDa, 50 kDa, or 20 kDa. Exemplary procedures for preparing low molecular weight hyaluronan are provided in WO 2011/156445. As discussed above, the molecular weight of the hyaluronan can be modified by cleaving hyaluronan with an acid or base to produce lower molecular weight hyaluronan. In certain aspects, the hyaluronan starting material or a derivative thereof is not derived from an animal source. In these aspects, the hyaluronan can be derived from other sources such as bacteria. For example, a recombinant $B.\ subtilis$ expression system can be used to produce the hyaluronan starting material.

After the low molecular hyaluronan or hyaluronan oligosaccharide has been treated with a base, it is reacted with a sulfating agent to produce the partially or fully sulfated hyaluronan. Sulfating agents commonly used in organic synthesis can be used herein. Examples of sulfating agents include, but are not limited to, pyridine-sulfur trioxide complex, chlorosulfonic acid, or the triethylamine-sulfur trioxide complex. In one aspect, low molecular hyaluronan or hyaluronan oligosaccharide can be converted to the tributylamine salt, lyophilized, resuspended in dimethylformamide, and subsequently treated with a sulfating agent (e.g., pyridine-sulfur trioxide complex) to sulfate one or more hydroxyl protons.

In one aspect, when the sulfating agent is a pyridine-sulfur trioxide complex, a pyridinium adduct of the sulfated hyaluronan is produced, where pyridine is covalently attached to the sulfated hyaluronan. Not wishing to be bound by theory, when hyaluronan is reacted with the pyridine-sulfur trioxide complex in a solvent such as, for example, DMF, a small amount of acid is produced from traces of water present in situ, which causes partial depolymerization resulting in a free reducing end group. The hydroxyl group of the hemiketal can ultimately be sulfated to produce a sulfated intermediate, which subsequently reacts with free pyridine produced in situ to produce the pyridinium adduct. Thus, the sulfated hyaluronan used herein can include a mixture of sulfated hyaluronan that does not have pyridine covalently attached to the molecule and sulfated hyaluronan that does have pyridine covalently attached to the molecule. In one aspect, from 0.01% to 100%, 0.1% to 10%, or 0.15% to 2.5% of the sulfated hyaluronan has pyridine covalently attached to the molecule. In another aspect, the molecular weight of the pyridinium adduct of the sulfated hyaluronan is less than or equal to 10 kDa. In other aspects, the molecular weight is 0.1 kDa, 0.5 kDa, 1 kDa, 2 kDa, 3 kDa, 4 kDa, 5 kDa, 6 kDa, 7 kDa, 8 kDa, 9 kDa, or 10 kDa, where any value can for the lower and upper end-point of a molecular weight range.

In another aspect, the modified hyaluronan is hyaluronan or its pharmaceutically acceptable salt or ester having at least one sulfate group and at least one primary C-6 hydroxyl position of an N-acetyl-glucosamine residue comprising an alkyl group or fluoroalkyl group.

In one aspect, at least one primary C-6 hydroxyl proton of the N-acetyl-glucosamine residue of hyaluronan is substituted with an alkyl group. The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. In one aspect, the alkyl group is a $C_1$-$C_{10}$ branched or straight chain alkyl group. In a further aspect, the alkyl group is methyl. The alkyl group can be unsubstituted or substituted. In the case when the alkyl group is substituted, one or more hydrogen atoms present on the alkyl group can be replaced with or more groups including, but not limited to, alkynyl, alkenyl, aryl, halide, nitro, amino, ester, ketone, aldehyde, hydroxy, carboxylic acid, aralkyl, or alkoxy.

In another aspect, at least one primary C-6 hydroxyl proton of the N-acetyl-glucosamine residue of hyaluronan is substituted with a fluoroalkyl group. The term "fluoroalkyl group" as used herein is a branched or unbranched saturated hydrocarbon group of 1 to 24 carbon atoms, wherein at least one of the hydrogen atoms is substituted with fluorine. In certain aspects, the fluoroalkyl group includes at least one trifluoromethyl group. In other aspects, the fluoroalkyl group has the formula —$CH_2(CF_2)_nCF_3$, wherein n is an integer of 1, 2, 3, 4, 5, 6, 7, 8, 9, or 10. In one aspect, the fluoroalkyl group is —$CH_2CF_2CF_3$ or —$CH_2CF_2CF_2CF_3$.

In one aspect, the methylated/sulfated hyaluronan has the formula depicted below:

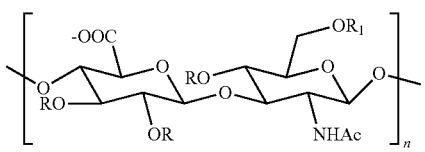

where $R_1$ is a methyl group, while the remaining R groups are sulfate groups alone or in combination with hydrogen. In one aspect, the n is from 5 to 20, 5 to 15, 5 to 10, or 7 to 9.

In another aspect, the modified hyaluronan can be a mixture composed of a first methylated/sulfated hyaluronan and a second methylated/sulfated hyaluronan with pyridine covalently bonded to the methylated/sulfated hyaluronan can be used in the methods described herein.

In one aspect, the mixture includes (a) a first modified hyaluronan or a pharmaceutically acceptable salt or ester thereof, wherein said first modified hyaluronan or its pharmaceutically acceptable salt or ester comprises (i) at least one primary C-6 hydroxyl proton of at least one N-acetyl-glucosamine residue substituted with a methyl group, (ii) an average molecular weight from 1 kDa to 15 kDa, (iii) a degree of methylation greater than 0 to 0.5 methyl groups per disaccharide unit; and (iv) a degree of sulfation of 2.5 to 4.0 sulfate groups per disaccharide unit; and (b) a second modified hyaluronan or a pharmaceutically acceptable salt or ester thereof, wherein said second modified hyaluronan or its pharmaceutically acceptable salt or ester comprises (i) at least one primary C-6 hydroxyl proton of at least one N-acetyl-glucosamine residue substituted with a methyl group, (ii) an average molecular weight from 1 kDa to 15 kDa, (iii) a degree of methylation greater than 0 to 0.5 methyl groups per disaccharide unit; and a (iv) degree of sulfation of 2.5 to 4.0 sulfate groups per disaccharide unit, wherein pyridine is covalently bonded to the second modified hyaluronan or a pharmaceutically acceptable salt or ester thereof.

In one aspect, the degree of methylation in the first and second modified hyaluronan is 0.030, 0.050, 0.075, 0.100, 0.125, 0.150, 0.175, 0.200, 0.225, 0.250, 0.275, 0.300, 0.325, 0.350, 0.375, 0.400, 0.425, 0.45, 0.475, or 0.500 methyl groups per disaccharide unit, where any value can be a lower and upper endpoint of a range (e.g., 0.030 to 0.300, 0.100 to 0.200, etc.). In one aspect, only the primary C-6 hydroxyl proton of an N-acetyl-glucosamine residue of the first and second modified hyaluronan is substituted with the methyl group (i.e., methyl group is only at this position). In other aspects, 1% to 100% 5% to 100%, 10% to 100%, 20% to 100%, 50% to 100%, 60% to 100%, 70% to 100%, 80% to 100%, 90% to 100%, or 95% to 100% of the primary C-6 hydroxyl protons of the N-acetyl-glucosamine residue of the first and second modified hyaluronan are replaced with a methyl group.

In another aspect, the first and second modified hyaluronan have an average molecular weight 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, or 15 kDa, where any value can be a lower and upper endpoint of a range (e.g., 1 kDa to 10 kDa, 3 kDa to 7 kDa, etc.).

In another aspect, the first and second modified hyaluronan have a degree of sulfation of 2.5, 2.75, 3.00, 3.25, 3.50, 3.75, or 4.00 sulfate groups per disaccharide unit, where any value can be a lower and upper endpoint of a range (e.g., 1.5 to 3.5, 3. to 4.0, etc.).

In another aspect, the amount of pyridine in the mixture of the first and second modified hyaluronan is 0.10, 0.25, 0.50, 0.75, 1.00, 1.25, 1.50, 1.75, 2.00, 2.25, 2.50, 2.75, 3.00, 3.25, 3.50, 3.75, or 4.00 wt % of the mixture, where any value can be a lower and upper endpoint of a range (e.g., 0.500 to 3.00, 1.00 to 2.00, etc.). The amount of pyridine can be quantified by $^1H$ NMR and UV spectroscopy.

In another aspect, the degree of methylation in the first and second modified hyaluronan is 0.03 to 0.3 methyl groups per disaccharide unit, the first and second modified hyaluronan has an average molecular weight from 1 kDa to 10 kDa, the degree of sulfation in the first and second modified hyaluronan is 3.0 to 4.0 sulfate groups per disaccharide unit, and the amount of pyridine present in the composition is from 0.1 wt % to 4.0 wt % of the composition.

The hyaluronan starting material can exist as the free acid or the salt thereof. Derivatives of hyaluronan starting material can also be used herein. The derivatives include any modification of the hyaluronan prior to the alkylation or fluoroalkylation step. A wide variety of molecular weight hyaluronan can be used herein. In one aspect, the hyaluronan has a molecular weight greater than 10 kDa prior to alkylation or fluoroalkylation. In another aspect, the hyaluronan has a molecular weight from 25 kDa to 1,000 kDa, 100 kDa to 1,000 kDa, 25 kDa to 500 kDa, 25 kDa to 250 kDa, or 25 kDa to 100 kDa prior to alkylation or fluoroalkylation. In certain aspects, the hyaluronan starting material or a derivative thereof is not derived from an animal source. In these aspects, the hyaluronan can be derived from other sources such as bacteria. For example, a recombinant *B. subtilis* expression system can be used to produce the hyaluronan starting material.

The hyaluronan starting material or derivative thereof is initially reacted with a sufficient amount of base to deprotonate at least one primary C-6 hydroxyl proton of the N-acetyl-glucosamine residue. The selection of the base can vary. For example, an alkali hydroxide such as sodium hydroxide or potassium hydroxide can be used herein. The concentration or amount of base can vary depending upon the desired degree of alkylation or fluoroalkylation. In one aspect, the amount of base is sufficient to deprotonate at least 0.001% of the primary C-6 hydroxyl protons of the N-acetyl-glucosamine residue of the hyaluronan starting material or derivative thereof. In other aspects, the amount of base is sufficient to deprotonate from 0.001% to 50%, 1% to 50% 5% to 45%, 5% to 40%, 5% to 30%, 5% to 20%, 10% to 50%, 20% to 50%, or 30% to 50% of the primary C-6 hydroxyl protons of the N-acetyl-glucosamine residue of the hyaluronan starting material or derivative thereof. It is understood that the more basic the solution, the more likely are chain cleavage reactions and the higher the degree of alkylation/fluoroalkylation that can be achieved. For example, other hydroxyl groups present on hyaluronan (e.g., 2-OH and/or 3-OH can be alkylated or fluoroalkylated). In one aspect, all of the hydroxyl groups present on hyaluronan can be alkylated or fluoroalkylated. In other aspects, 0.001%, 0.01%, 0.1%, 1%, 5%, 10%, 20%, 30%, 40%, 50%, 60%, 70%, 80%, 90%, 95%, 100%, or any range thereof of hydroxyl protons present on hyaluronan can be deprotonated and subsequently alkylated or fluoroalkylated.

After the hyaluronan starting material or derivative thereof has been treated with a base, the deprotonated hyaluronan is reacted with an alkylating agent or fluoroalkylating agent to produce the modified hyaluronan. Examples of alkylating agents include, but are not limited to, an alkyl halide. Alkyl bromides and iodides are particularly useful. Similarly, the fluoroalkylating agent can include a fluoroalkyl halide. Alkylating agents and fluoroalkylating agents commonly used in organic synthesis can be used herein.

In certain aspects, it is desirable to sulfate the alkylated or fluoroalkylated hyaluronan described above. In one aspect, the alkylated or fluoroalkylated hyaluronan is sulfated by reacting the alkylated or fluoroalkylated SAGE with a sulfating agent to produce a sulfated product. The degree of sulfation can vary from partial sulfation to complete sulfation. In general, free hydroxyl groups present on the alkylated or fluoroalkylated hyaluronan or a derivative thereof can be sulfated. In one aspect, at least one C-2 hydroxyl proton and/or C-3 hydroxyl proton is substituted with a sulfate group. In another aspect, the degree of sulfation is from 0.5, 1.0, 1.5, 2.0, 2.5, 3.0, 3.5 or any range thereof per disaccharide unit of the alkylated or fluoroalkylated hyaluronan. In one aspect, the alkylated or fluoroalkylated SAGE can be treated with a base to deprotonate one or more hydroxyl protons followed by the addition of the sulfating agent. The sulfating agent is any compound that reacts with a hydroxyl group or deprotonated hydroxyl group to produce a sulfate group. The molecular weight of the hyaluronan can vary depending upon reaction conditions. In one aspect, the molecular weight of the SAGE is from 2 kDa to 500 kDa, 2 kDa to 250 kDa, 2 kDa to 100 kDa, 2 kDa to 50 kDa, 2 kDa to 25 kDa, or from 2 kDa to 10 kDa.

In one aspect, the alkyl group of the SAGE is methyl and at least one C-2 hydroxyl proton and/or C-3 hydroxyl proton of hyaluronan is substituted with a sulfate group. In another aspect, the alkyl group of the SAGE is methyl, at least one C-2 hydroxyl proton and/or C-3 hydroxyl proton of hyaluronan is substituted with a sulfate group, and the compound has a molecular weight of 2 kDa to 200 kDa after alkylation.

Any of the sulfated and alkylated/fluoroalkylated hyaluronan useful herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)$NH_2$, —(CO)NHR and —(CO)$NR_2$, where R is an alkyl group defined above, can be prepared by reaction of the carboxylic acid-containing compound with ammonia or a substituted amine. Also, the esters can be fatty acid esters. For example, the palmitic ester has been prepared and can be used as an alternative esterase-activated prodrug.

The modified hyaluronan described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. For example, the pH of the composition is from about 5 to about 6, which is suitable for topical applications. Additionally, the pharmaceutical compositions can include carriers, thickeners, diluents, preservatives, surface active agents and the like in addition to the compounds described herein.

The pharmaceutical compositions can also include one or more active ingredients used in combination with the modified hyaluronan described herein. The resulting pharmaceutical composition can provide a system for sustained, continuous delivery of drugs and other biologically-active agents to tissues adjacent to or distant from the application site. The biologically-active agent is capable of providing a local or systemic biological, physiological or therapeutic effect in the biological system to which it is applied. For example, the agent can act to control and/or prevent infection or inflammation, enhance cell growth and tissue regeneration, control tumor growth, act as an analgesic, promote anti-cell attachment, reduce alveolar bone and tooth loss, inhibit degeneration of cartilage and weight bearing joints, and enhance bone growth, among other functions. Additionally, any of the compounds described herein can contain combinations of two or more pharmaceutically-acceptable compounds. Examples of such compounds include, but are not limited to, antimicrobial agents, anti-inflammatory agents, anesthetics, and the like. Methods for using these compositions as drug delivery devices is described in detail below.

The pharmaceutical compositions can be prepared using techniques known in the art. In one aspect, the composition is prepared by admixing a modified hyaluronan with a pharmaceutically-acceptable compound and/or carrier. The term "admixing" is defined as mixing the two components together so that there is no chemical reaction or physical interaction. The term "admixing" also includes the chemical reaction or physical interaction between the compound and the pharmaceutically-acceptable compound. Covalent bonding to reactive therapeutic drugs, e.g., those having nucleophilic groups, can be undertaken on the compound. Second, non-covalent entrapment of a pharmacologically active agent in a cross-linked polysaccharide is also possible.

Third, electrostatic or hydrophobic interactions can facilitate retention of a pharmaceutically-acceptable compound in the compounds described herein.

The modified hyaluronan can be administered in a number of ways depending on whether local or systemic treatment is desired, and on the area to be treated. Administration can be topically (including ophthalmically, vaginally, rectally, intranasally, orally, buccally, otologically, or directly to the skin or a mucosal membrane). Formulations for topical administration can include ointments, lotions, creams, gels, drops, suppositories, sprays, liquids and powders. Conventional pharmaceutical carriers, aqueous, powder or oily bases, thickeners and the like can be necessary or desirable. Administration can also be directly into the lung by inhalation of an aerosol or dry micronized powder.

The modified hyaluronan can also be injected parenterally either intravenously, subcutaneously, intramuscularly, intradermally, intranasally, intrathecally, subdermally, or by inhalation. In other aspects, the modified hyaluronan is administered rectally by an enema, suppository, catheter, needleless syringe, or bulb syringe. In another aspect, the modified hyaluronan is formulated as an aerosol, micronized powder, spray, wash, lavage, or other suitable formulations typically used in nasal applications or administration by inhalation. In another aspect, the modified hyaluronan or the pharmaceutically acceptable salt or ester thereof is administered intratumorally using techniques known in the art.

It will be appreciated that the actual preferred amounts of the modified hyaluronan in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999). For example, when administered intravenously the dosage of the modified hyaluronan can be from 25 mg/kg to 500 mg/kg. In another aspect, when administered orally the dosage of the modified hyaluronan can be from 500 mg/kg to 3,000 mg/kg. In another aspect, when administered topically the dosage of the modified hyaluronan can be from 1 w/v to 20% w/v. In another aspect, the modified hyaluronan or a pharmaceutically acceptable salt or ester thereof is administered to the subject in the amount of 0.1 mg/kg to 500 mg/kg per single dose, 3 mg/kg to 300 mg/kg per single dose, or 10 mg/kg to 100 mg/kg per single dose.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process.

Materials and Methods

Animals and Animal Husbandry

SCC-25-Luc2 cell tumor study: Six to eight weeks old male immune deficient NCr-nude (NCr-Fox1$^{nu/nu}$) mice were purchased from Taconic Biosciences (Rensselaer, NY) and kept at an environmentally controlled facility with a 12-hr light/dark cycle. Mice were housed in filtered cages with sterile Bed-o'-Cobs® bedding. Sterile food (LabDiet® 5053) and water were freely accessible. After a minimum 3-day acclimatization period, all animals were examined for their health and suitability for the study.

FaDu cell tumor study: Sixty, male CD1 nude mice were purchased from Charles River (UK) at 4-6 weeks of age and allowed to acclimatize for 2 weeks. All animals were held in individually ventilated cages (IVCs) in a SPF (Specific Pathogen Free) barrier unit. Animals were identified by ear punch in cages labelled with the appropriate information necessary to identify the study, dose, animal number and treatment groups. The animals were fed Rat and Mouse Expanded diet from B & K. Both feed and water were available ad libitum. Animal health was monitored daily. Cages were cleaned and bedding changed at regular intervals. There was a constant room temperature of 21±2° C. and a mean relative humidity of 55%±10%. The day-night cycle was constant with light and dark phases of 12 hours each starting at 7 a.m. and 7 p.m., respectively.

Drug

The methylated/sulfated hyaluronan (referred to below as GM-1111) was synthesized using the following procedures.

Preparation of Low Molecular Weight Hyaluronan

1. Slowly dissolve 20 g of 850 kDa HA (1% w/v) into 1.7 L of ddH$_2$O while vigorously stirring over heat (~40° C.). When all 20 g of HA is added, remove from heat and stir until cooled to room temperature, then slowly add 333 mL 6N HCl while stirring. Stir at room temperature for approximately 2 weeks.
2. Use HPLC, GPC, or SEC to monitor degradation reaction at 14 days. Neutralize each sample before analysis to stop reaction and analysis by UV detection at 232 nm, comparing to previous batches of methylated/sulfated hyaluronan.
3. At the molecular weight range of 3-5 kDa, neutralize the reaction to pH 7.0 by slowly adding 40% (w/v) NaOH over ice.
4. Dialyze in 1000 MWCO dialysis tubing against ddH$_2$O for 24 hrs, changing the water every 6 hrs to obtain hyaluronan fragments of greater than 1 kDa.
5. Lyophilize to obtain a white, fluffy solid. Yield: 12.032 g, 60.2%

Preparation of Methylated Hyaluronan

1. Dissolve 6.0 g (4% w/v HA in NaOH solution) of low molecular weight hyaluronan in 150 mL of a 40% w/v solution of NaOH in ddH$_2$O, and stir the mixture for 2 hours at room temperature, which generates a viscous solution.
2. Add 225 mL of isopropanol and continue stirring.
3. Add 6 mL (6 eq) of iodomethane, and stir the mixture for 24 hours at room temperature.

4. After 24 hours, use a separation funnel to remove the organic solvent layer from the viscous aqueous layer, and add 300 mL of ddH$_2$O to dilute the crude methylated hyaluronan.
5. Adjust the solution to pH 7.0 with 6N HCl on ice.
6. Allow the neutralized solution to warm to room temperature, and add 3 L of MeOH:EtOH (1:2 v/v) while stirring to precipitate the methylated hyaluronan intermediate. Collect the product by filtration, and dry it in a vacuum oven.

Sulfation of Methylated Hyaluronan to Produce GM-1111
1. Add 2.5 g of crude methylated hyaluronan to 200 mL of anhydrous DMF and stir for 1 h prior to adding 1.56 mL of tributylamine (1 eq). Stir the solution for 20 min at room temperature.
2. Add 25 g of pyridine-sulfur trioxide (24 eq.) by adding 5 g at a time.
3. Stir the mixture for 3 h at 40° C.
4. Cool the reaction on ice, and add 50 mL of ddH$_2$O to quench the reaction.
5. Precipitate the crude material by adding 250 mL of cold 95% ethanol saturated with anhydrous sodium acetate.
6. Centrifuge the crude product at 4,500 rpm for 5-10 min, and decant the liquid to collect the light brown gummy solid.
7. Dissolve the crude product in ddH$_2$O, and dialyze against 20 L of 100 mM NaCl, changing the solution four times a day over 24 h, followed by dialysis against 20 L of distilled water 4 times over 24 h.
8. Lyophilize the dialyzed material. Final Yield: 42.0% of methylated/sulfated hyaluronan (GM-1111)

The methylated/sulfated hyaluronan had the following characteristics: average molecular weight is 3 kDa to 7 kDa; average methyl groups per disaccharide unit is 0.3 to 0.3; average degree of sulfation of 3.0 to 4.0; and average pyridine content is 0.1 to 4.0 wt % (pyridine content used in experiments below is 0.69 wt %).

Tumor Cell Culture and Implantation

SCC-25-Luc2 cells (human tongue squamous cell carcinoma expressing a Luc2 luciferase reporter gene) were cultured below confluency according to American Type Culture Collection (ATCC) recommendations: a 1:1 mixture of DMEM and Ham's F12 medium containing 1.2 g/L sodium bicarbonate, 2.5 mM L-glutamine, 15 mM HEPES and 0.5 mM sodium pyruvate, and supplemented with 400 ng/mL hydrocortisone and 10% fetal bovine serum (DMEM: F12+10% FBS) and standard 1× penicillin/streptomycin. Cells were trypsinized for passaging and for implantation. To implant the tumor cells in the animals, SCC-25-Luc2 cells were displaced with trypsin and a single cell suspension at 10$^7$ cells/mL of serum free DMEM:F12 medium was prepared. 0.1 mL of tumor cells (10$^6$ cells) were then inoculated into the front tip of the tongue under isoflurane anesthesia.

The FaDu cells (human pharyngeal squamous cell carcinoma) were defrosted and cultured in DMEM supplemented with 10% FBS, L-glutamine (2 mM), penicillin (100 U/ml) and streptomycin (100 μg/ml). On Day −7, 5×10$^6$ FaDu cells were injected subcutaneously (s.c.) into the left flank of 60 mice using a 25 G needle in an injection volume of 100 μl per mouse. The s.c. implantation and subsequent tumor volume measurements, drug treatment and the injection of anesthetic were conducted in a class II cabinet.

Experimental Groups and Drug Administration

SCC-25-Luc2 cell tumor: Animals were inoculated with tumor cells on pre-randomization day 0 (Day PR0; estimated Day (−20)). When the mean total radiance flux (TRF) of tumors was measured at ~8×10$^7$ ph/s, the animals in Groups 1-4 were randomly distributed into four treatment groups consisting of a minimum of ten animals each, with animals in each group bearing tumors of similar mean TRF range. Randomization day was considered Day 0 of the study. Two separate groups (5 and 6) of animals were treated with vehicle (Group 5) or GM-1111 (Group 6) from the day of tumor cell implantation until the day before the experiment. The animals in Group 5-6 were not randomized and consisted of eight animals per group.

GM-1111 was prepared for dosing by dissolving the dried powder form of GM-1111 in phosphate buffered saline (PBS) at a concentration of 6 mg/mL. The animals in Group 5 were administered with vehicle (PBS, 5 mL/kg) and the animals in Group 6 were administered with GM-1111 (30 mg/kg). Both Groups 5 and 6 were treated once daily from Day PR0 (Day −17) to Day −1. Groups 1 and 3 were administered with vehicle and Groups 2 and 4 were administered with GM-1111, once daily from Day 1 to 20. Both vehicle and GM-1111 were administered subcutaneously (s.c.) in the back of the animal.

FaDu cell tumor: On Day −7 after tumor cell implantation, 20 mice were randomized into 2 groups of 10 to receive PBS (Group 1) or GM-1111 at 30 mg/kg (Group 2) daily via subcutaneous injection using a dose volume of 5 ml/kg. On Day 0, (seven days after tumor cell implantation), the remaining 40 mice were randomized based on tumor volume into 4 groups of 10 animals so that the mean tumor volume per group was 115-124 mm$^3$. Mice in Groups 3 and 5 received daily injections of PBS as control vehicle and mice in Groups 4 and 6 were administered daily GM-1111 at 30 mg/kg. PBS and GM-1111 were administered subcutaneously in the abdominal area using a dose volume of 5 ml/kg.

Tumors in Groups 5 and 6 were irradiated with 2Gy on five consecutive days (Mon-Fri) whereas Groups 3 and 4 were sham irradiated (i.e. anesthetized and placed into the restraints but not irradiated).

IVIS Imaging for Tumor Volume Measurement

SCC-25-Luc2 cell tumor: Following tumor cell inoculations, tumor growth was monitored in each animal by imaging with the Lumina Series III In-Vivo Imaging System (IVIS; PerkinElmer), two times each week. Tumor volume was determined by measuring the total radiance flux (TRF; photons/second (ph/s)). On the day of imaging, animals were administered with 150 mg/kg (body weight) D-luciferin substrate via intraperitoneal (i.p.) injection. Whole body imaging was done about 15-20 min after luciferin injection.

FaDu cell tumor: Once treatment started, mice were weighed daily and tumors were measured with calipers three times per week from Day 0.

Radiation Therapy

SCC-25-Luc2 cell tumor: On Day 0, the animals in Groups 3-4 were anesthetized with xylazine (5 mg/kg)/ketamine (100 mg/kg) by intraperitoneal (i.p.) injection. Prior to the irradiation, the mice were placed on a 4-mm polymethyl methacrylate plate. A lead shield with a small window cut-out of the top was placed over the animal to shield the rest of the body of the animal while exposing the area of the tumor in the tongue. Tumor targeted ionizing radiation was generated with a 160 kVp (15-ma) X-ray source at a focal distance of 30 cm, hardened with a 0.35 mm Cu filtration system at a rate of 3.2Gy/minute (30 Gy). The animals were monitored as they recovered from the anesthesia on a heated pad and returned to their home cage.

FaDu cell tumor: Animals were irradiated with 2Gy each day for 5 days using an XStrahl RS320 X-ray set, operated at 300 kV, 10 mA. The X-ray tube has additional filtration to give a radiation quality of 2.3 mm Cu half-value layer (HVL). Mice were anesthetized by intraperitoneally (i.p.) injecting ketamine (Vetquinol, France) and Rompun/Xylazine (Bayer, UK) and were placed into a plexiglass jig positioned at a distance of 700 mm from the focus of the X-ray tube. Radiation was delivered at a dose rate of 0.696Gy/min using a single uniform dose of radiation with the body being lead shielded except for a 1 cm hole in the lead above the tumor site. A dosimetry device (ion chamber) was placed in the irradiation chamber to confirm the dose received. The mean variance from the expected dose was 3.6%. After irradiation anesthesia was reversed by injecting Atipamezole s.c. (under the skin at the neck) and mice were returned to the IVCs.

Animal Welfare Thresholds and Supportive Care

Body weight changes as well as the general health of the animals were monitored daily. To help food intake, the animals were provided with highly palatable soft food. Supportive care in the form of sterile saline fluids were administered once daily by s.c. if animals lost more than 15% of their initial body weights, or twice daily if the body weight loss was over 20%. Animal welfare thresholds were set to trigger euthanasia and endpoint collection if the body weight loss was over 30%, if the tumor reaches 1000 mm$^3$ (FaDu cell tumor), if animals were unable to eat or drink water, or if any animal was observed to be in pain, distress, or was moribund. All procedures were followed by Biomodels's IACUC approved (18-0619-1) procedures (SCC-25-Luc2 tumor study) and certified according to the UK Animal (Scientific Procedures) Act 1986 (FaDu tumor study). The Office of Laboratory Animal Welfare (OLAW) assurance number of Biomodels is A4591-01.

Histological Examination

At the end of the experiment (day 21), the front half of the tongue tissues were longitudinally cut and fixed in 4% formalin. Excised FaDu cell tumors were fixed with Carnoy's fixative. Fixed tissues were then processed for paraffin embedding and sectioned at 3-4 μm thickness. Paraffin sections were stained with hematoxylin and eosin (H&E). Prepared slides were examined under microscope.

Data Analysis

All measured tumor volume (total radiance flux, TRF) data were expressed as mean and standard error of mean. The mean differences between and among the groups were determined by Student's t-test (Group 5 and 6) and one-way analysis of variance (ANOVA) test followed by Dunnett's t-test as post hoc multiple comparison test (Groups 1 through 4 in SCC-25-Luc2 cell tumor study) or Tukey's multiple comparison test (FaDu cell tumor study).

Results and Discussion

GM-1111 Enhances the Irradiation-Induced Tumor Regression

To investigate whether GM-1111 affected cancer therapy negatively, immune compromised NCr-nude (NCr-Foxn1$^{nu/nu}$) mice were orthotopically implanted with human squamous cell carcinoma cells expressing luc2 luciferase reporter gene (SCC-25-Luc2). When the tumor reached its target average size (TRF approximately 8×10$^7$ ph/s), two groups of animals were irradiated once with x-rays (30 Gy) to induce tumor regression while receiving either GM-1111 (30 mg/kg, s.c., once daily) or its vehicle from 24 hrs after the irradiation until the day before the end of the experiment. Two additional groups of animals were also treated with GM-1111 or vehicle without irradiation as controls. For the next 3 weeks, the size of the tumor was monitored twice a week by measuring the TRF in the body.

A week after the irradiation, the tumor in the x-ray/GM-1111 treatment group was noticeably smaller than in the no x-ray/vehicle treatment group (FIG. 1). The tumor regression in the x-ray/GM-1111 group continued for the remaining time of the experiment, and the decrease was statistically significant from day 10 until the end of the experiment. The tumor regression in the x-ray/GM-1111 is remarkable because the tumor in the x-ray/vehicle treatment group was slightly smaller than the no x-ray/vehicle treatment group and the significant changes were noted only on day 17. In addition, unlike the vehicle treatment group, the x-ray irradiation with GM-1111 treatment group resulted in full tumor regression. The synergistic effects of GM-1111 with the x-ray irradiation on the tumor were unexpected and noteworthy, as treatment with GM-1111 without x-ray irradiation did not lead to a significant decrease of the tumor's size in the animals.

Figure 2:
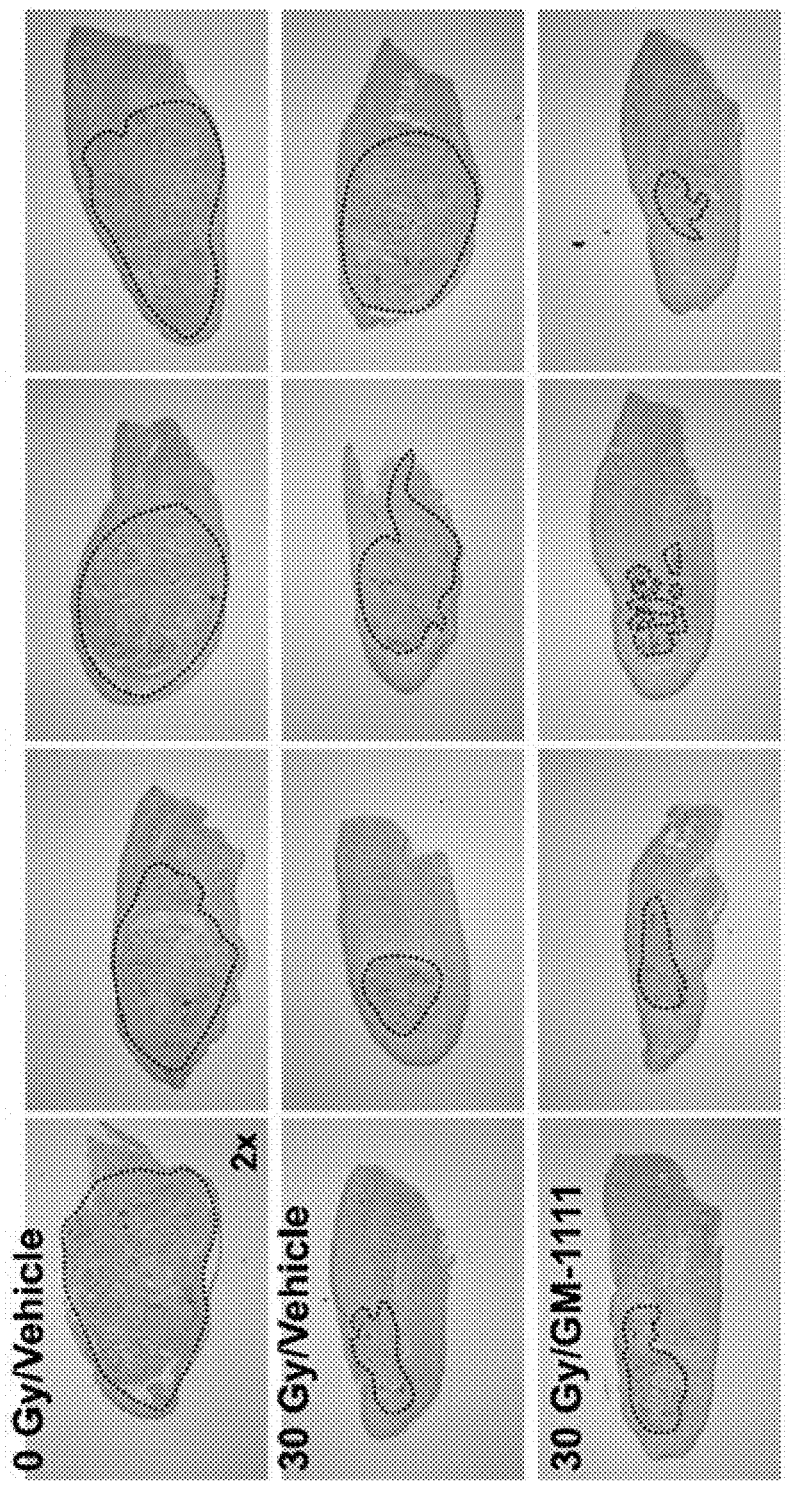
FIG. 2 shows microscopical images (hematoxylin and eosin stain, original magnification 2×) of tongue tissues implanted with SCC-25-Luc2 cells. Areas with developed tumor are illustrated with dotted lines. Front-half of the tongue tissues were taken at the end of the study (day 21) for histological examinations. The tissues from x-ray irradiated animals demonstrate the tumor regression compared to the tissues from the unirradiated control animals.

Histological examination of tongue tissues harvested at the end of the study confirmed irradiation-induced tumor regression (FIG. 2) as well as the significant effects of GM-1111 in enhancing irradiation-induced tumor regression. Compared to the unirradiated vehicle treatment control group, the area occupied by the tumor tissues were markedly reduced in the x-ray irradiation groups (dotted area in FIG. 2) and these tumors in the 30 Gy/GM-1111 treatment group appeared much smaller than the 30 Gy/vehicle treatment group.

Figure 3:
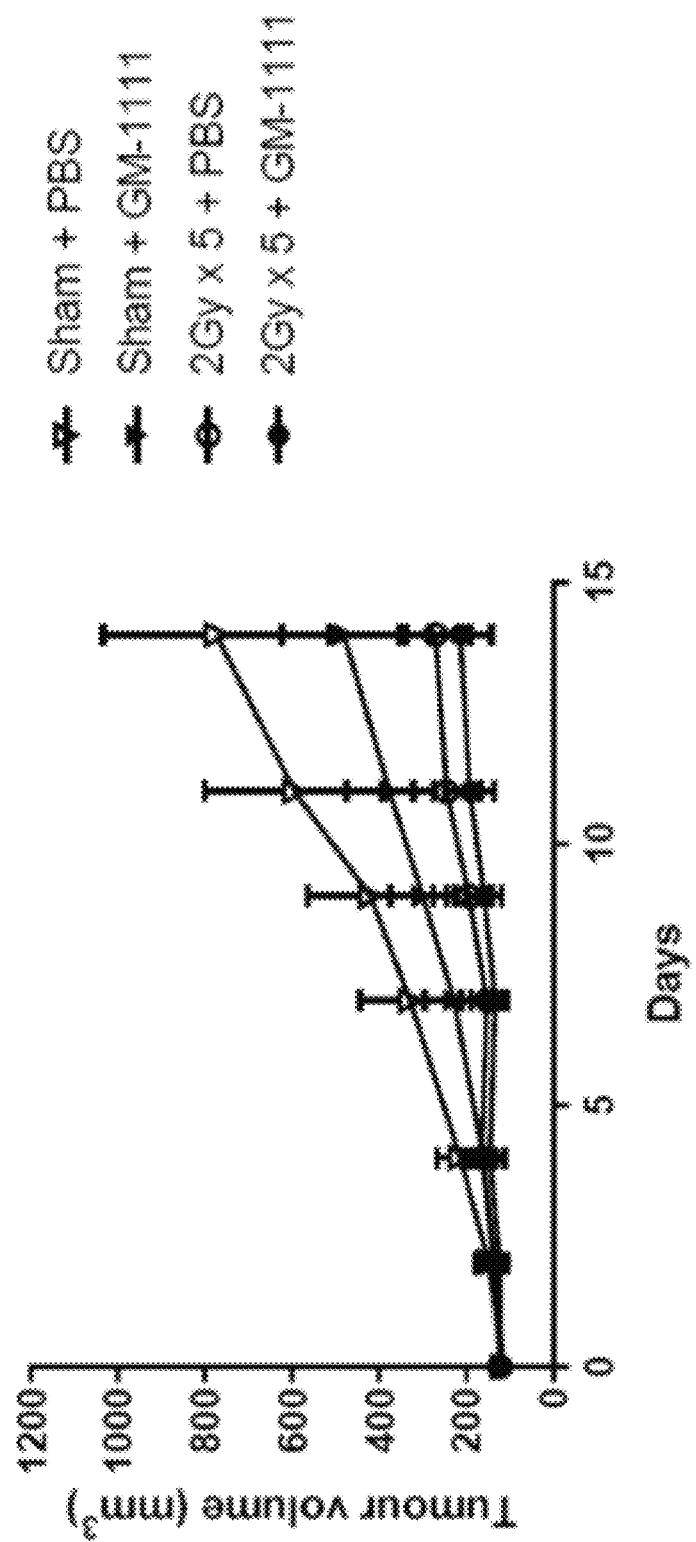
FIG. 3 shows changes of the volume of human pharyngeal tumor (FaDu cells) measured with calipers. Both GM-1111 (30 mg/kg) and vehicle were administered subcutaneously once daily from day 0 to day 14. Significant reduction of tumor volume was observed in GM-1111 alone, GM-1111 plus irradiation, and PBS plus irradiation group. Symbols and error bars represent mean±SD.
Figure 4:
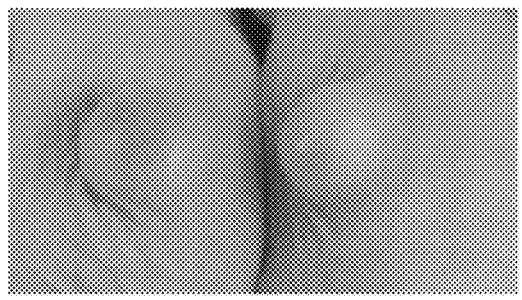
FIG. 4 shows the representative images of human pharyngeal tumors (FaDu cells) grown in the back of mice. Both GM-1111 (30 mg/kg) and vehicle (PBS) were administered subcutaneously once daily from day 1 to day 13.
Figure 4:
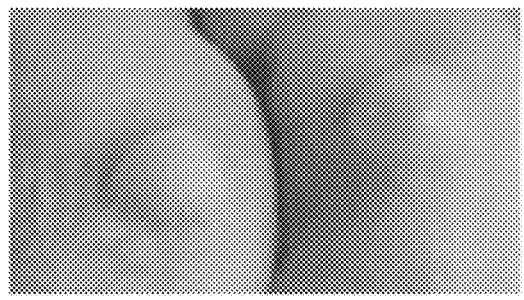
Figure 4:
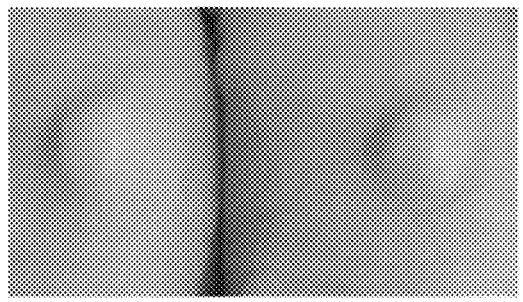
Figure 4:
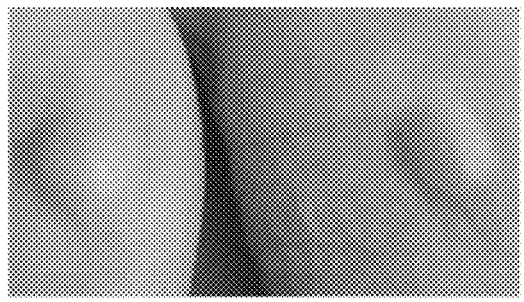

To test these anti-tumor or radiation enhancement effects of GM-1111, another human tumor xenograft model was studied. FaDu cells were derived from human pharyngeal cancer. Male CD1 nude mice were heterotopically implanted with FaDu cells. These animals developed tumors that measured around 115-124 mm$^3$ within 7 days. Half of these animals were then received x-ray irradiation at a dosage of 2 Gy/day for 5 consecutive days from day 0 to day 4 and the other half of the animals were sham treated. For each radiation or sham irradiation treatment group, tumor bearing animals were subdivided into 2 groups to receive either GM-1111 or vehicle (PBS). Sham irradiated, PBS treated control tumors almost doubled in size (×1.8) over the first 4 days and were ×6.6 of starting volume by Day 14, when the study ended (FIGS. 3 and 4). Treatment with GM-1111 without irradiation resulted in significantly reduced tumor growth compared to the non-irradiated, PBS treated controls from Day 10 (p=0.0154 using mixed model analysis with Tukey's test for multiple comparisons) until the study ended on Day 14 (p=<0.001). Furthermore, the fractionated irradiation reduced the tumor growth to ×1.4 of starting volume on Day 4 and ×2.2 on Day 14 in the PBS treated group. As a result, the detection of further growth inhibition induced by the Test Item GM-1111 was difficult. However, there did appear to be a longer latent period (slower re-growth) in the irradiated, GM-1111 treated group.

The radiation enhancement effects of GM-1111 are unexpected, since previous studies of the similar drug RGTAs-OTR4131 (a heparin-mimetic polymer) did not show such radiation sensitizing effects [10]. Overall, these data suggest that GM-1111 can enhance the radiation's effects to induce tumor regression.

GM-1111 does not Affect Implanted Tumor Growth

Figure 5:
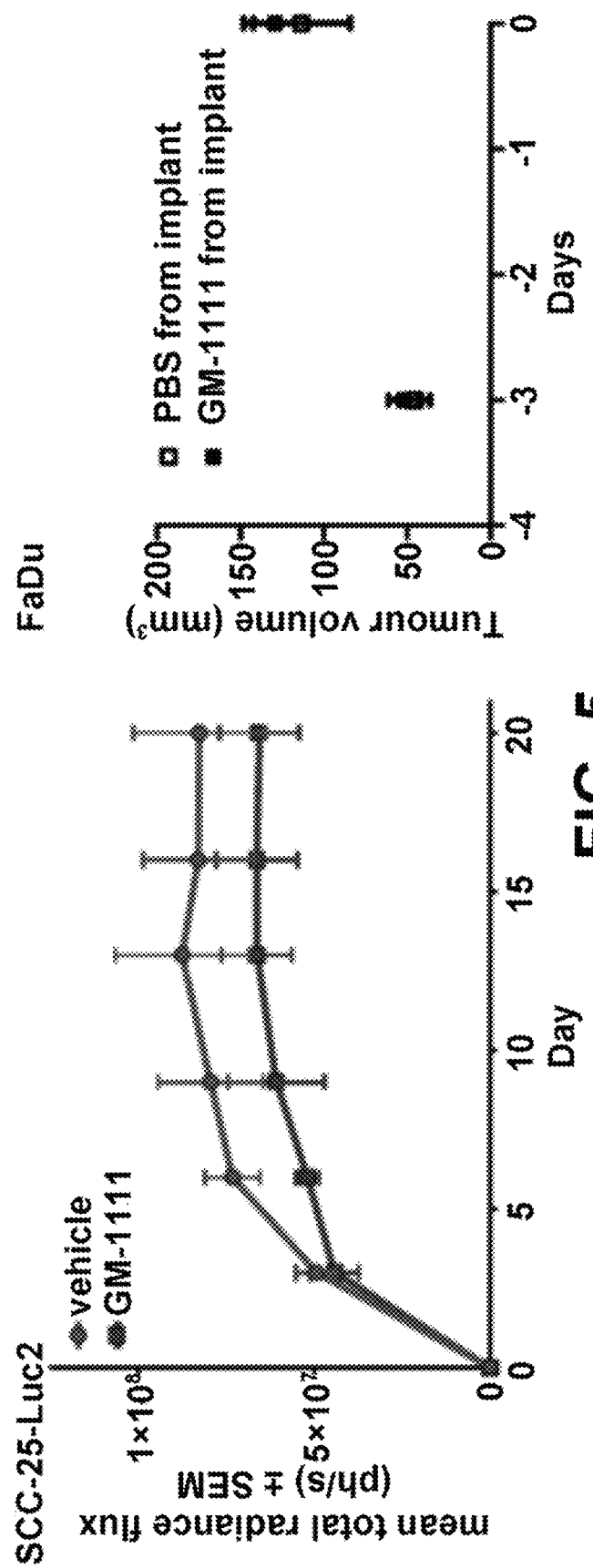
FIG. 5 shows the growth of tumor from implanted cancer cells (left panel: SCC-25-Luc2 cells; right panel: FaDu cells). Tumor volume was determined by measuring the luminescence (SCC-25-Luc2 cells) or with a caliper. Both GM-1111 (30 mg/kg) and vehicle were administered subcutaneously once daily from day of cell implant for 19 days (SCC-25-Luc2 cell tumor) or for 6 days (FaDu cell tumor). No significant reduction of tumor volume was observed in both tumor growth/establishment. Symbols and error bars represent mean±SEM (SCC-25-Luc2 cell tumor) or mean±SD.

In the previous experiment, GM-1111 enhanced tumor regression induced by x-ray irradiation. To further test whether GM-1111 could inhibit tumor growth and establishment without irradiation, GM-1111 was administered to a group of immune deficient nude mice (30 mg/kg, s.c., once daily) from 1 day after the implantation of SCC-25-Luc-2 cells in the front-end of the tongue. The tumor growth in these animals was compared with the tumor growth in animals administered with vehicle alone. While there was slightly decreased tumor growth in the GM-1111 treatment group on day 7 (p=0.34), no significant differences between the two groups were observed (FIG. 5 left). Also, nude mice implanted with FaDu cells were treated with either GM-1111 (30 mg/kg, s.c., once daily) or vehicle from the day of cell inoculation and observed the tumor growths. Similar to SCC-25-Luc-2 cell tumor studies, FaDu cell tumor growth was not interfered by GM-1111 administration (FIG. 5 right).

These data suggest that GM-1111 does not appear to directly inhibit the growth of implanted human tongue tumor cells.

CONCLUSION

The present study demonstrates that GM-1111 enhanced tumor regression when used with x-ray irradiation. These anti-tumor effects appear to be synergistic with radiation-induced cytotoxic effects as GM-1111 showed little effect on tumor growth without irradiation. From these data, GM-1111 has potential as a safe and effective radiation sensitizing drug that will induce tumor regression when used in combination with radiation therapy.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

REFERENCES

1. Rich J N. Cancer Stem Cells in Radiation Resistance. Cancer Res. 2007; 67: 8980-8984. doi:10.1158/0008-5472.CAN-07-0895
2. Skvortsova I, Debbage P, Kumar V, Skvortsov S. Radiation resistance: Cancer stem cells (CSCs) and their enigmatic pro-survival signaling. Semin Cancer Biol. 2015; 35: 39-44. doi:10.1016/j.semcancer.2015.09.009
3. Baumann R, Depping R, Delaperriere M, Dunst J. Targeting hypoxia to overcome radiation resistance in head & neck cancers: real challenge or clinical fairytale? Expert Rev Anticancer Ther. 2016; 16: 751-758. doi:10.1080/14737140.2016.1192467
4. Willers H, Azzoli C G, Santivasi W L, Xia F. Basic Mechanisms of Therapeutic Resistance to Radiation and Chemotherapy in Lung Cancer. Cancer J Sudbury Mass. 2013; 19: 200-207. doi:10.1097/PPO.0b013e318292e4e3
5. Liang H, Deng L, Hou Y, Meng X, Huang X, Rao E, et al. Host STING-dependent MDSC mobilization drives extrinsic radiation resistance. Nat Commun. 2017; 8: 1736. doi:10.1038/s41467-017-01566-5
6. Moergel M, Abt E, Stockinger M, Kunkel M. Overexpression of p63 is associated with radiation resistance and prognosis in oral squamous cell carcinoma. Oral Oncol. 2010; 46: 667-671. doi:10.1016/j.oraloncology.2010.06.012
7. Herscher L L, Cook J A, Pacelli R, Pass H I, Russo A, Mitchell J B. Principles of chemoradiation: theoretical and practical considerations. Oncol Williston Park N. 1999; 13: 11-22.
8. Lawrence T S. Chemotherapeutic agents as radiation sensitizers. Cancer Res. 2004; 64: 1312-1312.
9. Seiwert T Y, Salama J K, Vokes E E. The concurrent chemoradiation paradigm—general principles. Nat Clin Pract Oncol. 2007; 4: 86-100. doi:10.1038/ncponc0714
10. Mangoni M, Yue X, Morin C, Violot D, Frascogna V, Tao Y, et al. Differential Effect Triggered by a Heparan Mimetic of the RGTA Family Preventing Oral Mucositis Without Tumor Protection. Int J Radiat Oncol. 2009; 74: 1242-1250. doi:10.1016/j.ijrobp.2009.03.006

What is claimed:

1. A method for reducing or maintaining the size of a tumor in a subject, the method comprising exposing the tumor to ionizing radiation and administering subcutaneously or intravenously to the subject a pharmaceutical composition comprising a modified hyaluronan or a pharmaceutically acceptable salt or ester, wherein the modified hyaluronan or its pharmaceutically acceptable salt or ester comprises hyaluronan with at least one primary C-6 hydroxyl position of an N-acetylglucosamine residue substituted with a methyl group, and at least one C-2 hydroxyl proton, at least one hydroxyl proton, or at least one C-3 hydroxyl proton and at least one hydroxyl proton is substituted with a sulfate group, and the modified hyaluronan or its pharmaceutically acceptable salt or ester has an average molecular weight of 2 kDa to 10 kDa.

2. The method of claim 1, wherein the pharmaceutically acceptable salt is selected from the group consisting of $NH_4^+$, $Na^+$, $Li^+$, $K^+$, $Ca^{+2}$, $Mg^{+2}$, $Fe^{+2}$, $Fe^{+3}$, $Cu^{+2}$, $Al^{+3}$, $Zn^{+2}$, 2-trimethylethanolammonium cation, or a quaternary salt of isopropylamine, trimethylamine, diethylamine, triethylamine, tripropylamine, ethanolamine, 2-dimethylaminoethanol, 2-diethylaminoethanol, lysine, arginine, and histidine.

3. The method of claim 1, wherein the modified hyaluronan is administered to the subject after the tumor is exposed to ionizing radiation, before the tumor is exposed to ionizing radiation, or a combination thereof.

4. The method of claim 1, wherein the modified hyaluronan is administered to the subject while the tumor is exposed to ionizing radiation.

5. The method of claim 1 wherein the ionizing radiation comprises external beam radiation, brachytherapy radiation, or a combination thereof.

6. The method of claim 5, wherein the external beam radiation comprises radiation delivered from an ortho-voltage X-ray machine, a Cobalt-60 machine, a linear accelerator, a proton beam machine, a betatron radiation, a neutron beam machine, a gamma knife, spray radiation, stereotactic radiation, or any combination thereof.

7. The method of claim 5, wherein the brachytherapy radiation comprises interstitial radiation, intracavitary radiation, intraluminal radiation, radioligand tagged molecules administered intravenously, or any combination thereof.

8. The method of claim 1 wherein the modified hyaluronan or its pharmaceutically acceptable salt or ester has a degree of methylation from 0.03 to 0.50.

9. The method of claim 1 wherein the modified hyaluronan or its pharmaceutically acceptable salt or ester has from 50% to 100% of the primary C-6 hydroxyl protons of the N-acetyl-glucosamine residue of the modified hyaluronan are replaced with a methyl group.

10. The method of claim 1 wherein the modified hyaluronan or its pharmaceutically acceptable salt or ester has a degree of sulfation of 3.0 to 4.0 sulfate groups per disaccharide unit.

11. The method of claim 1 wherein the modified hyaluronan or its pharmaceutically acceptable salt or ester has an average molecular weight from 3 kDa to 7 kDa.

12. The method of claim 1 wherein the modified hyaluronan or its pharmaceutically acceptable salt or ester has an average molecular weight of 3 kDa to 7 kDa, a degree of methylation from 0.03 to 0.30, and a degree of sulfation of 3.0 to 4.0.

* * * * *